(12) United States Patent
Wong et al.

(10) Patent No.: US 10,037,820 B2
(45) Date of Patent: Jul. 31, 2018

(54) SYSTEM AND METHOD FOR MANAGING PAST, PRESENT, AND FUTURE STATES OF HEALTH USING PERSONALIZED 3-D ANATOMICAL MODELS

(71) Applicant: Medical Avatar LLC, New York, NY (US)

(72) Inventors: Virgil Wong, New York, NY (US); Jessica Lacson, Orlando, FL (US)

(73) Assignee: Medical Avatar LLC, Brooklyn, NY (US)

( * ) Notice: Subject to any disclaimer, the term of this patent is extended or adjusted under 35 U.S.C. 154(b) by 385 days.

(21) Appl. No.: 13/839,645

(22) Filed: Mar. 15, 2013

(65) Prior Publication Data

US 2013/0325493 A1    Dec. 5, 2013

Related U.S. Application Data

(60) Provisional application No. 61/689,161, filed on May 29, 2012.

(51) Int. Cl.
*G16H 50/20*    (2018.01)
*G16H 50/70*    (2018.01)
*G16H 50/50*    (2018.01)

(52) U.S. Cl.
CPC ............. *G16H 50/20* (2018.01); *G16H 50/50* (2018.01); *G16H 50/70* (2018.01)

(58) Field of Classification Search
CPC ........ G06Q 50/22–50/24; G16H 50/00–50/70; G06F 19/345–19/3443
See application file for complete search history.

(56) References Cited

U.S. PATENT DOCUMENTS

| 6,602,070 | B2 * | 8/2003 | Miller ..................... A61C 7/00 433/213 |
| 7,555,436 | B2 | 6/2009 | Brown |
| 8,146,005 | B2 | 3/2012 | Jones et al. |
| 9,101,261 | B2 * | 8/2015 | Kim .......................... A61B 5/00 |
| 2002/0007294 | A1 * | 1/2002 | Bradbury ............... G16H 15/00 705/2 |
| 2006/0089543 | A1 | 4/2006 | Kim et al. |

(Continued)

OTHER PUBLICATIONS

Behm-Morawitz, "Mirrored selves: The influence of self-presence in a virtual world on health, appearance, and well-being," http://www.sciencedirect.com/science/article/pii/S0747563212002269, Jan. 31, 2013.

(Continued)

*Primary Examiner* — Robert A Sorey
(74) *Attorney, Agent, or Firm* — Briggs and Morgan, P.A.; Daniel A. Rosenberg; Audrey J. Babcock

(57) ABSTRACT

A computer generated 3-D model of the human body (avatar) is created by aggregating personal health and medical data of a user. This data may include data derived from the user's electronic medical record. The user's physical characteristics are entered into the software to generate a personalized avatar that resembles him or her. Data regarding the user's medical history and physical characteristics are visualized on the avatar to map the past and present states of the user, and may be modified by a set of health variables for the purpose of projecting a future body image over established time intervals.

8 Claims, 24 Drawing Sheets

(56) References Cited

U.S. PATENT DOCUMENTS

| | | | |
|---|---|---|---|
| 2006/0127852 A1* | 6/2006 | Wen | A61C 7/00 433/213 |
| 2006/0278245 A1 | 12/2006 | Gan | |
| 2007/0126733 A1* | 6/2007 | Yang | G06F 3/011 345/419 |
| 2008/0146334 A1 | 6/2008 | Kil | |
| 2008/0319308 A1* | 12/2008 | Tang | A61B 5/055 600/416 |
| 2009/0044113 A1 | 2/2009 | Jones et al. | |
| 2009/0309891 A1 | 12/2009 | Karkanias et al. | |
| 2010/0106475 A1* | 4/2010 | Smith et al. | 703/11 |
| 2010/0172567 A1 | 7/2010 | Prokoski | |
| 2011/0077968 A1 | 3/2011 | Kelly et al. | |
| 2011/0301982 A1* | 12/2011 | Green et al. | 705/3 |
| 2012/0015316 A1* | 1/2012 | Sachdeva et al. | 433/24 |
| 2012/0127157 A1 | 5/2012 | Adler et al. | |
| 2012/0136218 A1 | 5/2012 | Lee et al. | |
| 2012/0182291 A1 | 7/2012 | Rawat et al. | |
| 2013/0011819 A1 | 1/2013 | Horseman | |

OTHER PUBLICATIONS

Dorner, S. "Design and development of a web application for mobile devices promoting a healthy lifestyle," http://www.hci4all.at/wordpress/wp-content/plugins/project_plugin/uploads/Dorner%20(2011)%20Masterthesis_WellnesManager_20110304sd.pdf, Mar. 31, 2011.

Kim, "Visualizing ideal self vs. actual self through avatars: Impact on preventive health outcomes," http://www.sciencedirect.com/science/article/pii/S0747563212000635, Jul. 31, 2012.

Wong, "Research on time travel simulations of personalized patient bodies for smoking cessation," http://virgilwong.com/research, Dec. 31, 2012.

International Search Report and Written Opinion for PCT/US2013/043173, dated Oct. 24, 2013.

* cited by examiner

SYSTEM AND METHOD FOR MANAGING PAST, PRESENT, AND FUTURE STATES OF HEALTH USING PERSONALIZED 3-D ANATOMICAL MODELS

RELATED APPLICATIONS

This application claims the benefit of priority of U.S. Provisional Patent Application No. 61/689,161, filed May 29, 2012, which is hereby incorporated by reference in its entirety.

TECHNICAL FIELD

The present invention relates to computer software for multiple platforms including but not limited to web, mobile, wearable technologies, holograms, game systems, motion-capture, TV, and other devices that allows people to create personalized interactive three-dimensional (3-D) anatomical models of themselves for visualizing, understanding, and managing their past, present, and future states of health.

BACKGROUND OF THE INVENTION

Cancer, heart disease, diabetes, obesity, and many other diseases are complex problems based on evolving systems—a combination of constantly-changing factors that encompass a range of solutions, probabilities not certainties, compounding effects, infinite interrelatedness, and sheer randomness. Obesity, for example, can be caused by a mixture of genetic, social, psychological, and environmental factors over time, which will likely never be "cured" by a magic pill or a shot in the arm.

What is needed to address evolving system problems is the transformation of people's mental models—the constructs and assumptions used to guide decision-making over a long period of time. Individuals with poor mental models often believe that they are invincible, have "good genes", or only need to think about health when they are sick. They may, for example, make bad decisions about diet, exercise, sleep, and smoking every day—and over years, develop life-threatening medical problems.

People with good mental models enjoy the compound effect of their good decisions. The present invention is designed based on a positive, evidence-based and health-behavior mental model: the personal and informed decision mental model. The invention guides health and medical-related decision-making by aggregating critical information about the past, present, and future in a personalized, engaging, and interactive way.

SUMMARY OF THE INVENTION

The present invention is directed to a computerized system and method for generating three-dimensional anatomical models of human bodies, which may be customized based on each user's physical characteristics and medical history. These three-dimensional anatomical models are referred to herein as "medical avatars." Three-dimensional anatomical models representing future body images (i.e. medical avatars showing a user's possible future appearance) may also be created based on various health-related variables.

In exemplary embodiments of the present invention, a computer generated 3-D model of the human body (medical avatar) is created by aggregating personal health and medical data over time from various sources, including an electronic medical record from the hospital or doctor's office. The user's physical characteristics are entered into the software to generate a medical avatar that resembles him or her. All of these parameters are visualized on the medical avatar to map the past and present states of the user—and then modified by a set of health variables for the purpose of projecting a future body image over established time intervals.

Medical data of various aspects, such as vital signs, health conditions, laboratory results, and diagnostic images, may be visualized in a 3-D anatomical display via a desktop or wearable computer, tablet, smartphone, game system, TV, or other device. Health conditions "map" to the various organ systems in the body. Utilizing the taxonomy in the index of medical subject headings, a visual relationship is generated between the health condition and the organ system. As the health condition may impact multiple organ systems in the body, the anatomical display has multiple layers such as skeletal, nervous and respiratory systems upon which information can be rendered. For a more detailed view, a zoom and rotation function provides the ability to manipulate the digital body with its various health conditions. The conditions and their related medical data can be more easily accessed and understood in this manner.

In one embodiment, the invention is directed to a method of presenting health-related information, the method being performed by execution of computer readable program code by at least one processor of at least one computer system. The method includes providing a three-dimensional anatomical model of a human which has a plurality of anatomical systems; creating a personalized anatomical model by altering an appearance of the three-dimensional anatomical model based on a physical attribute of a user; conducting a predictive analysis of a future health condition of the user based on data derived from a medical history of the user; and creating a future anatomical model by altering an appearance of at least one anatomical system based on a result of the predictive analysis. For example, the data used in the predictive analysis may include data relating to the user's diet and fitness routine, and the results of the predictive analysis may include the user's predicted weight, fat-lean ratio, and body mass index at a future date. A future anatomical model of the user may then be created which shows the predicted appearance of the user at the future date, based on the user's diet and fitness routine.

In another embodiment, the invention is directed to a method of presenting health-related information, the method being performed by execution of computer readable program code by at least one processor of at least one computer system. The method includes providing a three-dimensional anatomical model of a human which has a plurality of anatomical systems; creating a personalized anatomical model by altering an appearance of the three-dimensional anatomical model to include a physical attribute of a user, and by altering an appearance of at least one anatomical system based on a medical history of the user; attaching information regarding medical symptoms to the personalized anatomical model; and transmitting the personalized anatomical model to a health care provider for a medical diagnosis.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

In the accompanying drawings, which form part of the specification, like numerals and letters refer to like parts wherever they occur.

DETAILED DESCRIPTION OF THE INVENTION

In exemplary embodiments of the present invention, users can create personalized interactive 3-D anatomical models of themselves for visualizing, understanding, and managing their past, present, and future states of health. This digital anatomical visualization may include various functionalities that allow users to personalize their medical avatars, receive tailored content from their doctor or hospital, map information over a lifespan timeline, graph data, manage future health states, record "notes-to-self," share data, view their Continuity of Care document (CCD), import Health Level 7 (HL7) data, and visualize weight loss and fitness training.

Figure 1:
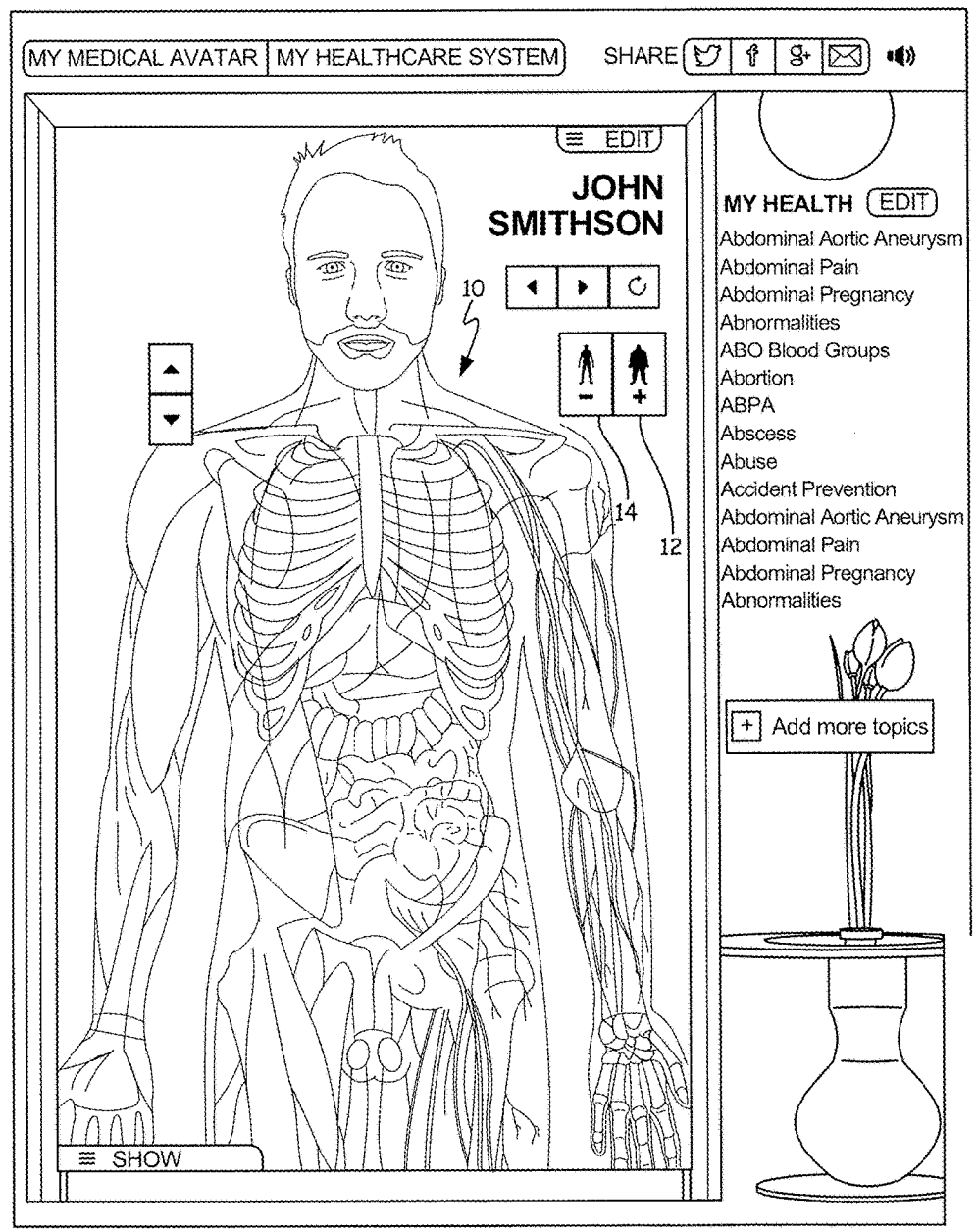
FIG. 1 is a screenshot showing the personalization of a body of a user's medical avatar, in accordance with the present invention.

FIG. 1 illustrates a display of the medical avatar application through which the body of the medical avatar 10 may be personalized. Body personalization of the medical avatar of the present invention has three main components: (1) customizable anatomical models, (2) user-made changes to the models based on data input directly by users, and (3) automatic changes to the models which can be based on data from a third party or an electronic medical record.

The customizable anatomical models may include default bodies for men and women of different ethnicities and ages, including children. Default medical avatars are avatars of healthy, idealized bodies. The digital models include morph targets, which allow for data inputs by the user or a third party to control the size and shape of polygons in the models. The software matches the name of each anatomical part of the model (or group of anatomical parts) to a specific controller that changes its x, y, z dimensions. These changes are limited by constraints established in the models to stay within human-plausible dimensions and proportions.

Users can make changes to these models based on data they input directly. Users can enter exact measurements of their body parts, including clothing sizes, so the medical avatar matches their current body dimensions. Or they can select a default 3-D anatomical body that most closely matches their own. Selections include gender, ethnicity, age, height, and body type.

Body types include the following (or a combination of the following): ectomorph, mesomorph, and endomorph.

In terms of age, users will see their bodies grow older over time. And they can "travel through time" to view their bodies at different ages via the software's timeline interface. The timeline interface is further discussed below, in connection with FIG. 7. The present invention includes customizable default models of bodies for different age groups, including pediatric bodies between ages 0-13, adolescent bodies between ages 13-19, young adult bodies between ages 20-40, older adult bodies between ages 41-64, and geriatric bodies for ages 65 and older.

Figure 2:
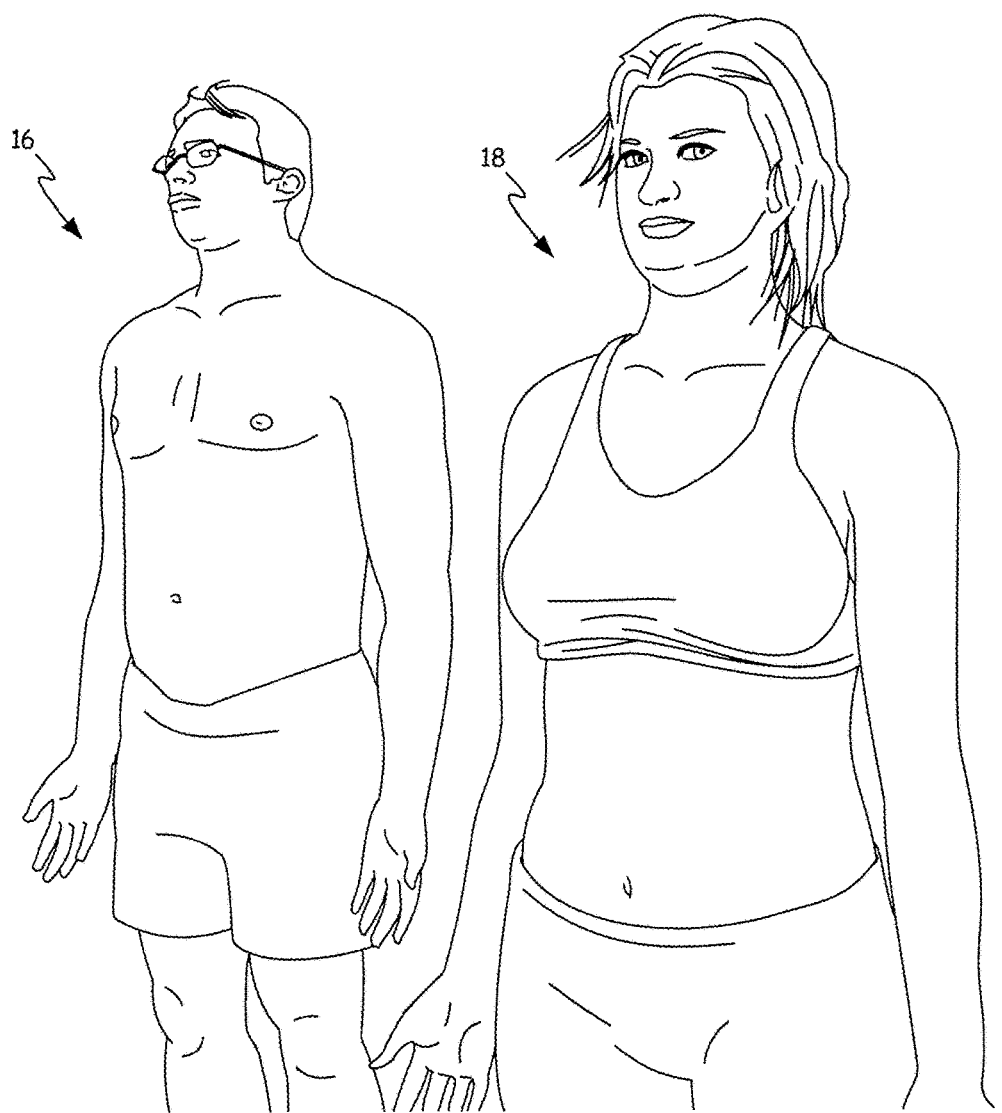
FIG. 2 is a depiction of male and female medical avatars.
Figure 3:
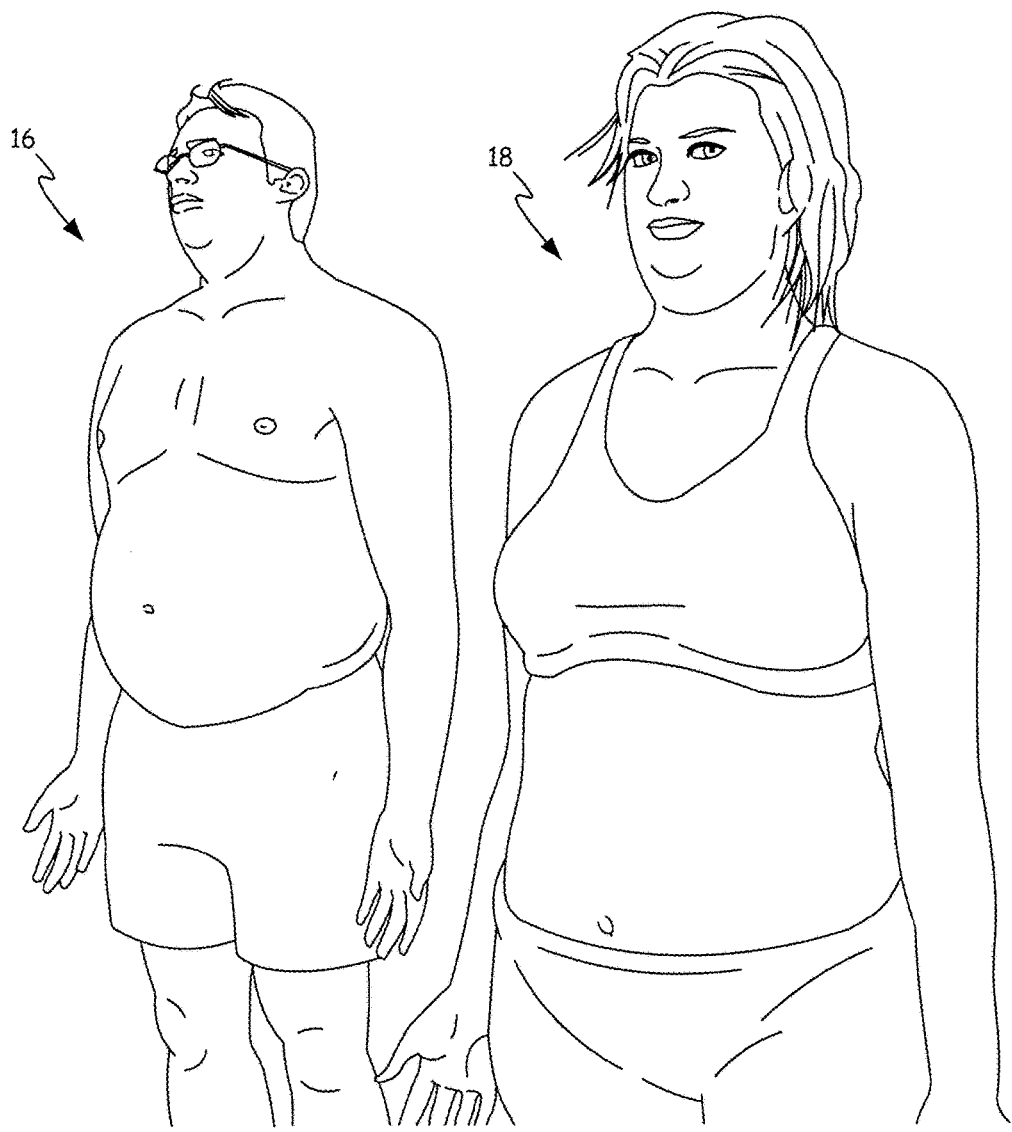
FIG. 3 is a depiction of the medical avatars of FIG. 2, after being altered to show increased body mass.
Figure 4:
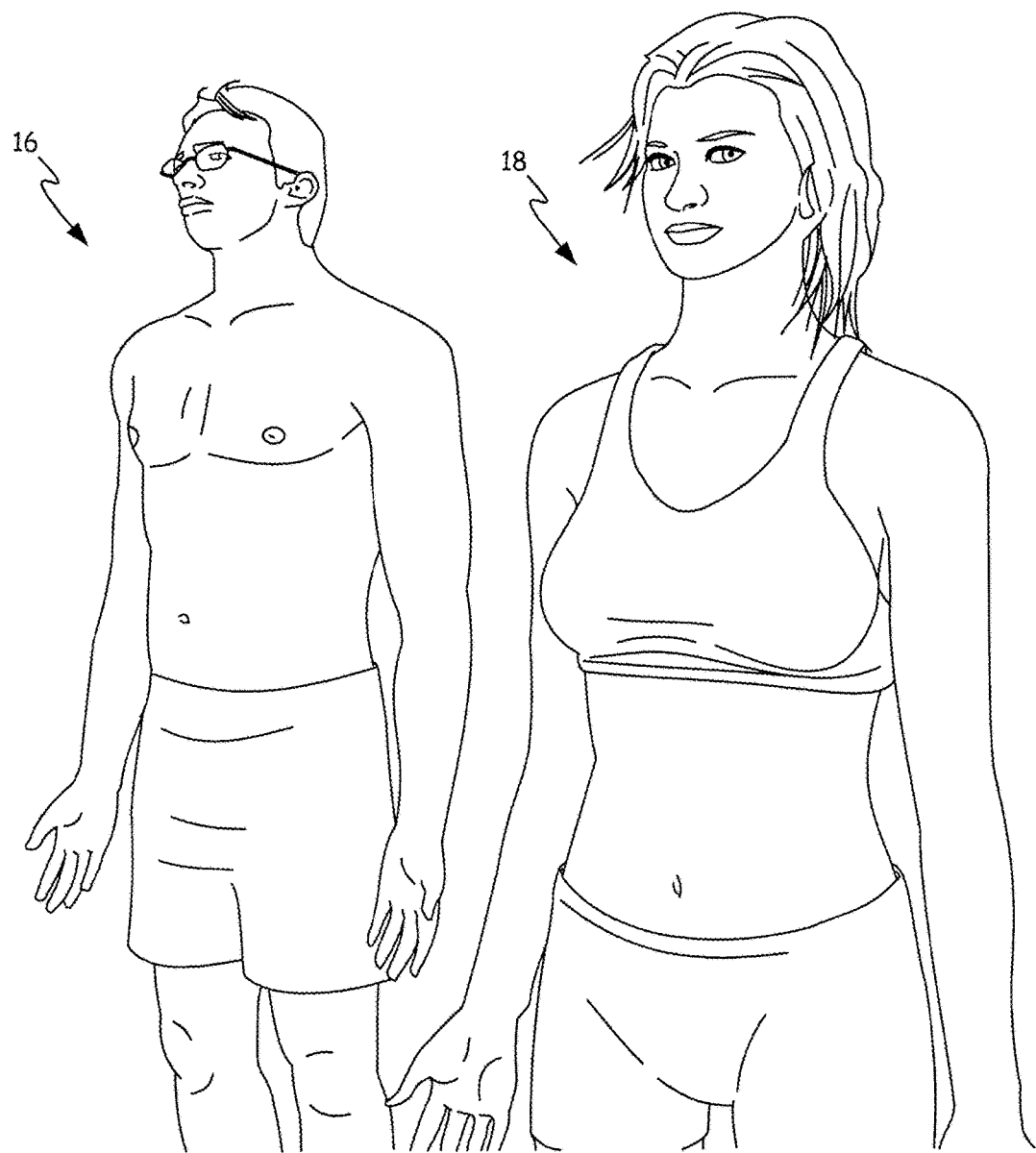
FIG. 4 is a depiction of the medical avatars of FIG. 2, after being altered to show decreased body mass.

Users can set a body type, or combination of body types, for their medical avatars. Users can modify their body shape, musculature, and amount of body fat for the medical avatar representing their current age or at different ages. For example, in the embodiment shown in FIG. 1, clicking or tapping the plus icon 12 increases the apparent body mass of the medical avatar, while clicking or tapping the minus icon 14 decreases the apparent body mass of the medical avatar. An example of possible male and female medical avatars 16, 18 are shown in FIG. 2. The medical avatars 16, 18 following alteration to show increased body mass are shown in FIG. 3. The medical avatars 16, 18 following alteration to show decreased body mass are shown in FIG. 4. Users may also see changes in their avatars over time based on diet and exercise, as further discussed below in connection with FIG. 9. In some embodiments of the present invention, the software allows users to manipulate the controllers for all the body parts of their medical avatars to match the size and shape of their own bodies—or to visualize desired improvements to their current bodies.

In some embodiments of the present invention, automatic changes to a medical avatar can be made based on data from a third party or an electronic medical record. If a medical avatar is not already present for a given patient, the available demographic and health information may predefine physical characteristics of the medical avatar, including but not limited to the patient's age, gender, height, weight, body type, fat-lean ratio, and body mass index.

A patient's medical avatar may be fully customized based on the patient's current health conditions, past medical history, and potential issues in the future. For example, diseased organs, tumors, injuries like broken bones and cuts, amputated limbs, prosthetics, medical implants, and cosmetic surgical changes can all be shown in the medical avatar.

The medical avatar may also show the patient what he or she can expect at various stages of care. For example, before a surgical procedure, a patient can navigate the medical avatar in a virtual environment to see what will happen when he or she arrives at the hospital, checks-in, goes to the operating room, receives anesthesia, wakes up, stays at the hospital, goes home, and follows post-discharge instructions. The virtual experience reduces stress and anxiety during the actual experience because the patient knows beforehand exactly what to expect.

In the virtual environment, patients can see procedures performed directly on their medical avatars as well as the possible results from treatment. For example, a patient considering bariatric surgery can witness a laparoscopic gastric bypass, gastric banding, duodenal switch, and sleeve gastrectomy performed on their medical avatar. The differences between the procedures are made apparent, and when the medical avatar eats a meal, the patient can see the resulting restriction in food consumption. Potential changes in weight over a specified time period, along with possible complications and other factors that may affect outcomes, are also shown on the medical avatar. The visualizations serve patient education purposes and help patients make informed decisions together with their care providers.

The medical avatar may be used to visualize the positive effects of treatment compliance and the potential negative effects of non-compliance. For example, patients who adhere to therapies for asthma, diabetes, and hypertension can see their healthy medical avatars leading productive lives. Non-compliant patients, however, are given a virtual preview of the complications and progression of disease that is likely to occur.

Figure 5:
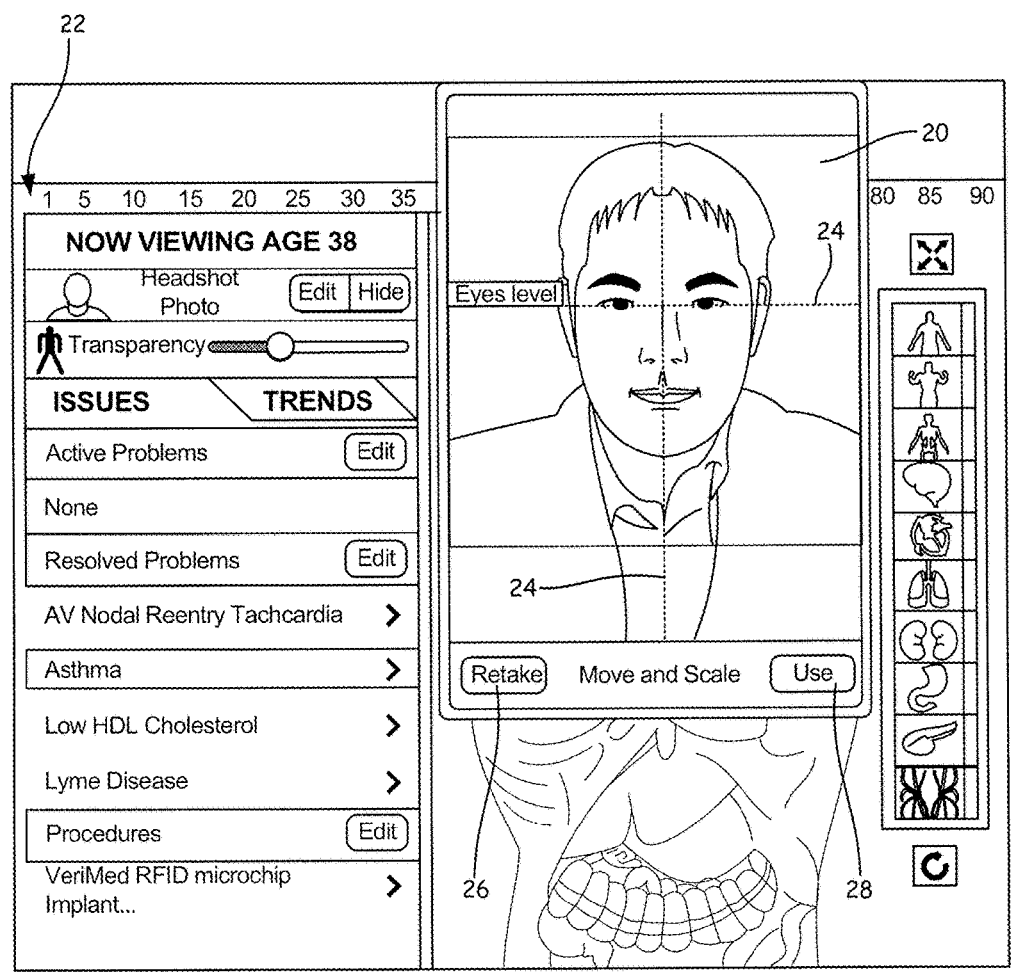
FIG. 5 is a screenshot showing medical avatar personalization using a headshot photograph of the user.

A medical avatar may be further personalized to reflect a user's physical characteristics, by using a photograph of the user's face to achieve facial personalization of the avatar. FIG. 5 illustrates facial personalization. Facial personalization may be performed using a headshot capture function of the software. In one example of a headshot capture function, headshot capture has two main components: 1) photo alignment and 2) 2-D to 3-D transformation.

The first component of headshot capture is photo alignment. A window 20 appears when clicking the button 22 in the screen display. First, the user takes two photos of himself or herself using the device's camera. The user must take a frontal photo of his or her face as well as a side profile photo. A front facing camera makes this process much simpler. If a front facing camera is not available, another individual may take the user's photograph.

Once the photos are taken, the user aligns specific pick points necessary for transformation of the 2-D images into a 3-D model. The following pick points are needed on the frontal face photo: center of the pupils, the outermost points on the nose flaps, corners of mouth, outermost points of the cheekbones, occluding contour of the jaw at the same height as the mouth (or what would be the same height if the face is tilted up or down). The following pick points are needed on the side profile photo: sellion, nose tip, halfway in-between on the nose bridge, outer corner of eye, where nose meets philtrum, forward-most point of upper lip, forward-most point of lower lip, forward-most point of chin, part-way between chin and neck on lower chin contour. The user drags each pick point to the proper location on their frontal and side profile photos. Once the user is done, the pick point data is saved and output to an XML file where the column and row counts start at (0,0) for the top left pixel of the image. Users may use this functionality to capture multiple photos over time to build a chronology of facial photos moving forward. Past facial photos can also be pulled from other sources outside of the application for alignment on the medical avatar at the specific ages when the photos were taken.

The second component of headshot capture is 2-D to 3-D transformation. This component uses the FaceGen SDK, which is available from Singular Inversions Inc. in Toronto, Ontario (www.facegen.com). The pick point data XML file is loaded into the invention. A head mesh topology along with parametric data is then generated in C++. Face controllers can manipulate the mesh topologies to simulate changes such as aging or obesity. Accessory models such as hair or glasses can be added as well. Shape statistics leave the neck seam unchanged for seamless stitching of the personalized face/head model to the rest of the medical avatar body. The invention also includes a custom tool that loads the resulting .OBJ format models into Cocos3D, which at the current time only supports PowerVR (.POD) format models. The custom loader is written as a subclass of 'CC3Resource', following the patterns of the 'CC3PODResouce' class. Cocos3D is an open source Objective-C framework used by the invention.

3-D models from radiographic imaging such as MRI, CT, PET, and microscopy can also be imported into the medical avatar. Picture archiving and communication systems (PACS) store grayscale and color images in DICOM, TIFF, Interfile, GIF, JPEG, PNG, BMP, PGM, RAW or other image file formats. Software such as 3D-DOCTOR can create 3D surface models and volume rendering from these 2-D cross-section images in real time. The resulting surface models in .OBJ format supplant the generic organ models in the medical avatar. For example, the personalized lung model made from CT replaces the generic lung model. The user can thus see a more naturalistic representation of his or her own pulmonary system. The radiographic models can also be used for patient education purposes. For example, a CT model of a longer-term smoker's lungs can be imported to motivate smoking cessation. Lung cancer diagnosis and progression can also be visualized to illustrate the potential positive effects of treatment and help promote patient compliance.

Figure 6:
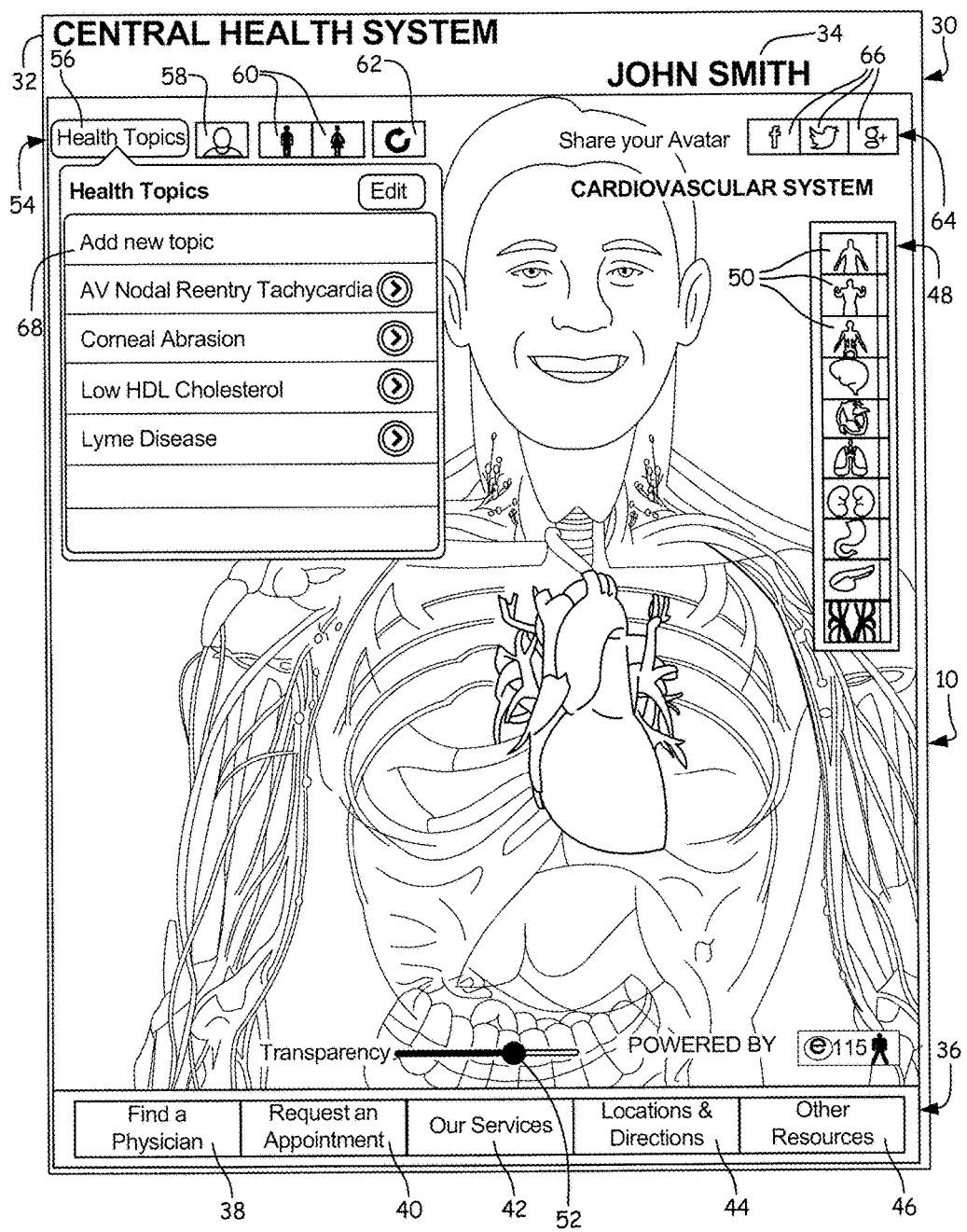
FIG. 6 is a screenshot of a medical avatar application customized for a specific hospital.

Medical avatar application software may be customized for specific providers and payers. FIG. 6 is a screenshot of a medical avatar application developed for a hospital which, for purposes of illustration, is referred to as Central Health System, which is a fictitious hospital. This screenshot includes a patient's medical avatar 10. In the embodiment described below, the custom hospital application has four main components: 1) a header with the hospital logo, 2) a footer with linkages to hospital web services, 3) a user-facing profile building tool, and 4) a messaging platform for sending broadcast messages. Other embodiments may include fewer main components, or more main components than the four discussed below.

The first component, a header 30, is used to represent the brand of the hospital by embedding the hospital logo 32 at the top of the application screen. To begin, the developer obtains the hospital logo to be used. Since logos vary in dimension, design and color, the developer must adjust the top portion of the screen to reflect these various elements. In one embodiment, the dimensions are as follows: 768×84 portrait, and 1024×84 landscape. In another embodiment, the logo dimension are 300×60. The background color may be changed to match the hospital logo and the actual logo design may be cropped to fit the dimensions of, for example, the top left portion of the screen.

The second component of the application, a footer, contains various buttons that can be adjusted depending on the hospital's needs and requirements. The number of buttons in the footer may vary in different embodiments, from one to as many buttons as may be represented in the footer. In the embodiment shown in FIG. 6, the footer contains five buttons. In some embodiments, the total characters of the button names may be limited. For example, in one embodiment, the total character length of all button names cannot exceed 91 characters.

Each of the buttons in the footer may match the hospital branding. The buttons contain links to information which the hospital chooses to display in conjunction with the medical avatar. These links may include links to a physician directory, a department directory, information regarding clinical services, information regarding administrative services, health content, multimedia/video content, recent health news, information regarding locations and directions, a page from which a patient may make an appointment, and any other resources or information. Depending on the links selected, the developer updates the labels of each of the buttons and embeds the link provided by the hospital. Once a user clicks on any of these buttons in the footer, the application redirects him or her to the appropriate website or function associated with the link.

In the example shown in FIG. 6, the following five hospital-specific buttons are included: "Find a Physician" 38, "Request an Appointment" 40, "Our Services" 42, "Locations & Directions" 44, and "Other Resources" 46. Each of these buttons provides a link to the associated website, or to the associated content from a page on a website (such as the hospital website), or to pages within the medical avatar application that contain content (such as content from the hospital). For example, the button 38 labeled "Find a Physician" may provide a link to a hospital's "Find a Physician" search page, formatted for smartphones and/or tablets. All of a hospital's physicians may be searchable through this page. The button 40 labeled "Request an Appointment" may provide a link to a hospital's "Request an Appointment" page, and the button 42 labeled "Our Services" may provide to a link to a hospital's comprehensive list of services, each formatted for smartphones and/or tablets. The "Locations & Directions" button 44 may provide a link to a list of a hospital's locations, with each address linked on an on-line map. The location addresses and map links may be pulled from hospital website. The "Other Resources" button 46 may provide a link to a web page including an index of links provided for the patient. The web page may be created on the hospital's content management system.

It is beneficial if a hospital for which a medical avatar application is created has a website administered by a content management system. Information for the application may then be pulled from the content management system. Moreover, hospital content updates or text corrections may be made by the hospital through its content management system. For example, all content updates may be made to the hospital website using the content management system. The content may then be pulled from the website to appear within the medical avatar application, to be accessed via the buttons in the footer.

The third component of the application, a user-facing profile builder, requires the end user to answer five demographic questions. The answers to these questions develop the basic setup of the user's personalized medical avatar. In one embodiment, the questions include: 1) first and last name, 2) date of birth, 3) gender, 4) email address, and 5) health topics of interest selected from a listing of clinical specialties provided. In other embodiments, fewer questions may be asked, or additional questions pertaining to the user may be asked.

The fourth component, a messaging platform, provides select members authorized by the hospital the capability of logging into a specific website and sending large-scale broadcast messages to their user base. The website functions similarly to a weblog platform and offers the ability to create messages with text, static images and multimedia videos as necessary. The authorized user is linked directly to the anonymous data collected from patients during the profile building phase and can create a patient cohort to send messages to based on demographic criteria. These criteria may include, but are not limited to, date of birth, gender, and health topics of interest. The messages sent to a patient cohort may include marketing messages.

Once the message is delivered to the patient's in-box, the patient may receive a notification through the application display. In one embodiment, the application display includes an icon or badge which indicates the number of messages in the user's in-box. Users may check these messages at their leisure by clicking on the in-box icon, which leads them to a message screen with a list of messages from their hospital. The message may include a call-to-action, such as an event registration, which will take the user to an external web page.

A user, such as an authorized hospital representative, can send or transmit text messages to patients based on various characteristics, such as the patients' indicated interests (e.g. heart disease, exercise, etc.) or demographics (e.g. age, gender, location, etc.).

Different anatomical systems may be viewed by clicking on a navigation bar 48, as shown in FIG. 6. The navigation bar contains a plurality of system buttons 50, with each system button corresponding to a different anatomical system. Each anatomical system may be viewed separately when clicking on each system button 50. Alternatively, the structures associated with the selected anatomical system may be highlighted in the medical avatar. In one embodiment, the medical avatar is organized into 13 anatomical systems: (i) eyes and vision; (ii) ear, nose, and throat; (iii) teeth and mouth; (iv) skin, hair, and nails; (v) bones and muscles; (vi) lungs and breathing; (vii) heart and blood; (viii) digestive; (ix) hormones; (x) urinary; (xi) reproductive; (xii) immune; and (xiii) brain and nerves.

The transparency of the anatomical systems of the medical avatar may be controlled using a slider 52, as shown in the display of FIG. 6. All visible anatomy may be made equally transparent, except for any highlighted organs or parts.

The user can easily rotate, zoom in, and zoom out of the medical avatar to view different anatomical systems and organs. On a touch interface, a finger swipe to the left or right will rotate the 3-D models. A two finger swipe zooms into the body, and a two finger pinch zooms out of the body.

The content management system may manage data entered by patients using the medical avatar application. In the present embodiment, the first step for the patient to generate a medical avatar is to enter relevant demographic information such as his or her first and last name, date of birth, gender, email address and health topics of interest. This data may be relayed directly to the hospital's content management system to be used for anonymous data analysis at a later time. The authorized hospital user may then log into the website provided to determine a patient cohort to whom to send messages. For example, female patients over 50 years old interested in diabetes represent one such possible patient cohort. After selecting the cohort, the authorized user may generate a broadcast message to these patients that would appear in their application's in-box. The patients would notice a number appear on the corner of their in-box icons indicating they have a specific number of messages from their hospital. Once a patient clicks on the in-box, the message appears in another screen for the patient to review.

The medical avatar application display may also include a control toolbar 54. In the present embodiment, the control toolbar includes five buttons, but other embodiments may include a different number of buttons in the toolbar. As shown in FIG. 6, the present embodiment includes the following buttons in the control toolbar: a health topics button 56, a photograph button 58, gender selection buttons 60, and a reset button 62.

The health topics button 56 allows patients to add any health topic in the medical avatar application library. Each topic is mapped to the anatomical body of the medical avatar 10. The health topics in the medical avatar application library may include an alphabetical and searchable listing of diseases and conditions.

The photograph button 58 allows patients to add photographs of themselves through the camera of the device running the medical avatar application, such as a desktop computer, laptop computer, tablet, or smartphone. In some embodiments, photographs of the patient are taken using the medical avatar application. In other embodiments, photographs of the patient obtained by, for example, a digital camera may be uploaded for use by the medical avatar application.

The gender selection buttons 60 allow patients to change the gender of a medical avatar, so that patients may use the application to look up information regarding diseases and conditions associated with either gender. When the male gender is selected, the application displays information regarding diseases and conditions associated with the male gender. When the female gender is selected, the application displays information regarding diseases and conditions associated with the female gender.

The reset button 62 returns the medical avatar to its original view. No data is lost when the reset button is activated.

The medical avatar application display may also include a sharing toolbar 64. For example, as shown in FIG. 6, the sharing toolbar may include buttons 66 associated with various social media sites, such as Facebook, Twitter, and Google+. Selecting these buttons allows users to share their medical avatars on the associated social media sites. The sharing toolbar may also include a button allowing users to email information regarding their medical avatars.

When users select a button 66 associated with a social media site, a message may appear, asking them to confirm that they wish to share the image of the medical avatar on the social media site. The information for possible sharing may be restricted such that only a screenshot image from the medical avatar application is shared, and no other functionality or information regarding the patient is provided to the social media site. When a medical avatar is shared on a social media site, the hospital's logo and a link to the hospital's website may also be provided.

A medical avatar application customized for a hospital may include specific content from the hospital, tailored for a patient. For example, selected content from the hospital website may appear in the application based on health topics selected by the patient. All content updates may be made to the website using the hospital's content management system. The content is then pulled from the hospital website to appear within the application, bridging the relationship between the patient and the hospital.

Any health or hospital-related content may be pulled from a website and included in the medical avatar application display, as set forth below in Table 1. For example, if a user selects a health topic from the drop-down menu 68 shown in FIG. 6, the resulting display may include a list of related services offered by the hospital, next to information regarding the selected health topic. The list of related services may include links to information regarding each service in the list. The display may also include a list of physicians from the hospital whose practice is related to the health topic selected by the patient. Both the service information and physician information may be obtained from the hospital's website content management system. Consumer health content may be pulled from sources such as the Krames Staywell Health Library or the MedlinePlus database from the U.S. National Library of Medicine.

TABLE 1

Personalized Content from Medical Avatar Interface

| Content | Input | Output | Server Side Configuration |
|---|---|---|---|
| Physicians | Keyword | Physician Name (with Prefix and postfix)<br>Link to Physician Profile | # of items to send to client |
| Services | Keyword | Service Name<br>Links to Service | # of items to send to client |
| Consumer Health Content | Keyword | Consumer Health Content Title<br>Link to content article | # of items to send to client |
| Multimedia/Video | Keyword | Link to Media File (Image or MP4 video)<br>Thumbnail Image<br>Media File Height<br>Media File Width<br>Length of the Video<br>Video Type (Youtube or MP4 or Image) | Media Auto Play Yes/No<br>May be limits to number of items that may be sent, such as a limit that only 1 item can be sent |
| Latest Health News | Keyword | Health News Title<br>Release Date<br>Link to Health News Article | # of items to send to client<br>Date Range from which to select |

In a preferred embodiment, the representational state transfer (REST) server responds in JavaScript Object Notation (JSON). Preferably, there is a method to request all the data in one single request or ask for individual items. The REST server may contain an input that contains an encrypted shared secret to verify that only the authorized client is calling the server. If the shared secret is wrong, the server will not even process the request.

Preferably, the client should try to reach the server three times consecutively. If the server is not available, the client should stop trying to reach the server until the next user clicks on the client.

WebView with CSS may be maintained on the server.

Figure 7:
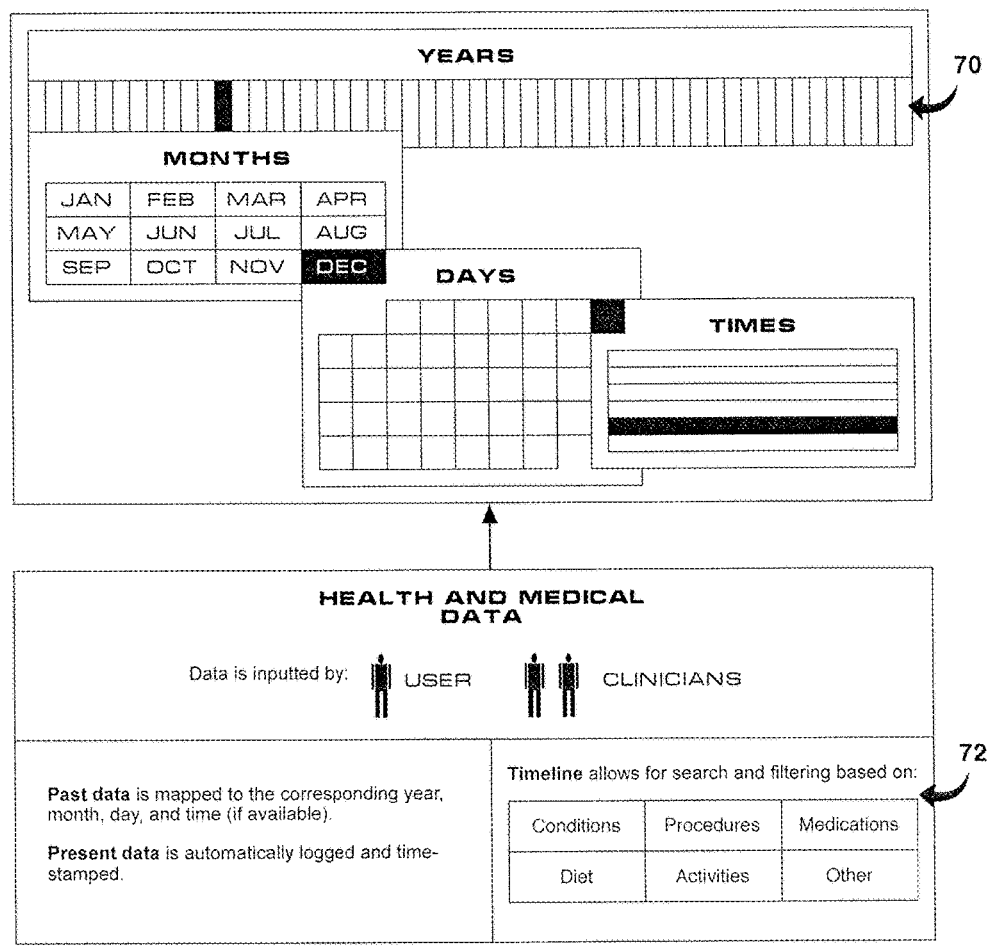
FIG. 7 is a chart depicting the timeline functionality of a medical avatar application.

FIG. 7 is a chart representing the timeline functionality of the medical avatar application. The timeline interface allows easy access to available health and medical information from any year, month, day, and/or time of the user's lifetime. The user's entire lifespan may be encompassed by the timeline. The timeline transforms the medical avatar to only display information and characteristics from the specified time period. The timeline interface has two main components: 1) a ticker bar with years, months, and days and 2) a filter for referring to a previous time or past input.

In one embodiment, the first component, a ticker bar 70, has vertical time indicators and a round scroll icon that allows a user to tap, hold and move to another date where a previous input was made. As a user can have multiple medical avatars for different time periods, the timeline offers the ability to go to each of those time periods with a simple motion of the finger.

The ticker bar 70 may be located anywhere on the display. For example, it may span the length of the screen just below the header but above the main digital anatomical medical avatar. The timeline's starting point is the user's current age and last input. From there, a user may scroll to another section of the timeline where an input was made. The inputs can be of any variety, such as, but not limited to, notes made by the user about symptoms on a specific date and time, a Continuity of Care Document which was input by the user or a third party, and any medication or procedure updates made by either the user or a third party. A timeline icon allows users to hide or show the timeline depending on their preference.

The second component of the timeline functionality is a filter 72 embedded within the timeline that allows a user to filter content based on search parameters, such as conditions, procedures, medications, diet, activities, symptom tags and any other types of notes the user has made. Once users submit a search query, they are provided with a list of results based on the search criteria. Upon clicking on a listed result, specific points in the timeline are highlighted to indicate exact dates and times. Users may then scroll to a specific date and time to review the desired content. In one embodiment, once the users have finished their filtered search, they may select "Done" in the list of results to default back to the original screen.

As a use-case example, if a user was diagnosed with diabetes in May of 2003 and suffered a heart attack in October of 2005, this medically related information would be inputted in the timeline either by the user or a third party such as a hospital staff member. By going to the particular date on the timeline, the user can view any medical data related to the health condition diagnosed or treated on that date. Any associated findings are recorded in a similar time-based fashion to provide a detailed chronology of the health conditions.

Additionally, a user can filter the timeline for a particular health condition by episode to track the entire timeline from beginning to end. For example, a user inputs the aforementioned diabetes diagnosis in May of 2003 with associated vital signs, laboratory results and diagnostic images. Subsequent visits to a doctor or hospital are recorded in the timeline that may or may not be related to the original diabetes diagnosis. If a user desires to view only the visits, results and medical data related to the diabetes diagnosis, an episodic view of that diagnosis can be rendered to display from start to present any or all information related to that diagnosis. The user can scroll to any of the highlighted portions to review the details of his or her diabetes-related inputs.

On the other hand, if the user wants to review medications only related to the heart attack in October of 2005, he or she may select this in the filtering criteria to display when any mention of that medication occurred within the timeline, and to review these inputs. In one embodiment, when the user has completed the filtering, the user may select "None" in the filtering criteria to eliminate the highlights and view the medical avatar from its default setting.

Figure 8:
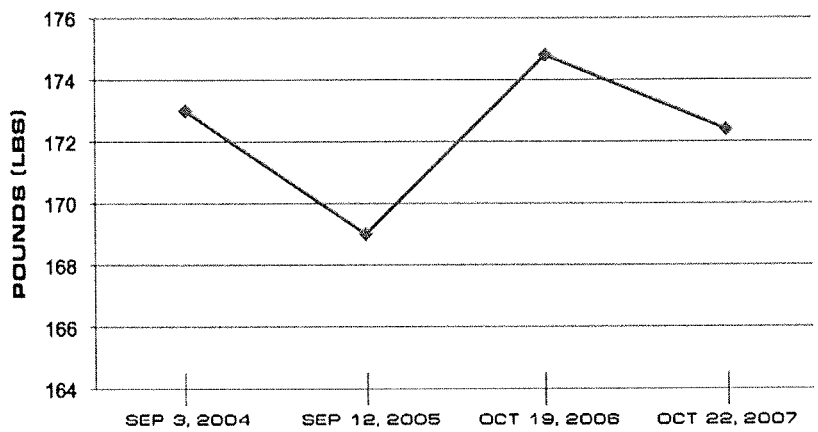
FIG. 8 shows graphs of a user's weight and body mass index (BMI) over time.
Figure 8:
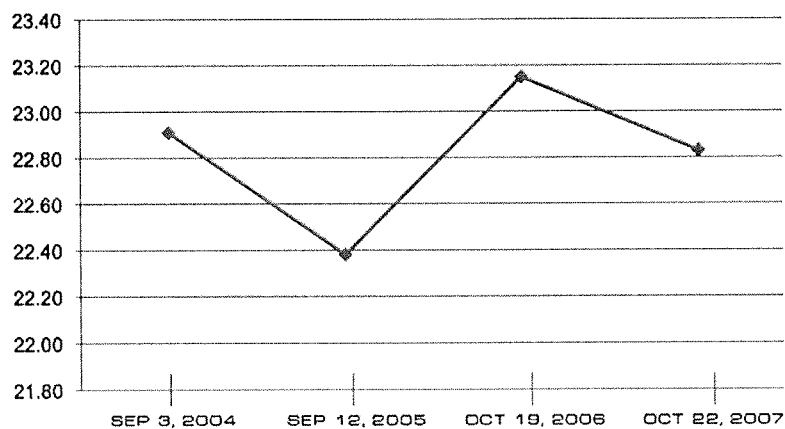

The filtering functionality of the timeline interface may be used to display data and trends related to specific health measurements. As shown in FIG. 8, the data may be displayed using graphs. The graphs in FIG. 8 are plots of a user's weight and body mass index (BMI) over time.

The primary function of data graphing is the ability of the user to view textual data in a graphical format. Laboratory and vital signs data is commonly displayed within tables with columns and rows indicating current values, past values, benchmark values and whether the patient is over and under the benchmark. Data graphing provides the ability to immediately view such data on a graph, such as a line graph, with an x-axis for time and a y-axis for the metric in question. The user can easily view the changing trends of such data over time using this format.

Data graphing requires the mapping of the discrete textual data inputted by the patient or provided by a third party to the x and y axis of the graph. The data may be stored as local JSON files and then, using a JavaScript graphing application programming interface (API), the data may be displayed graphically via the device's in-app web browser.

As a use-case example, if a user receives from another party laboratory or vital signs data, that data may be filtered from beginning to end in a line graph or diagram. For example, blood pressure from 2003-2006 can be depicted on a line graph with the year on the x-axis and the systolic and diastolic values on the y-axis. A benchmark line for systolic at 120 and diastolic at 80 can be drawn horizontally on the line graph to illustrate the patient's trends above and below this line, provide visual cues and guidance about when blood pressure was higher or lower than normal.

Similarly, weight readings from 2005-2010 inputted by the patient over that time period can be displayed on a line graph with the years on the x-axis and the weight values on the y-axis. If a user chooses to benchmark against a target weight, they may input this value into the benchmark box of the graph so they can analyze readings above and below that target.

If a user's height is known, a similar line graph can be easily generated for BMI as well. Such line graphs can be created for any input, such as, but not limited to, A1C test results, glucose levels, hematocrit levels, high-density lipoprotein (HDL) levels, and low-density lipoprotein (LDL) levels.

Figure 9:
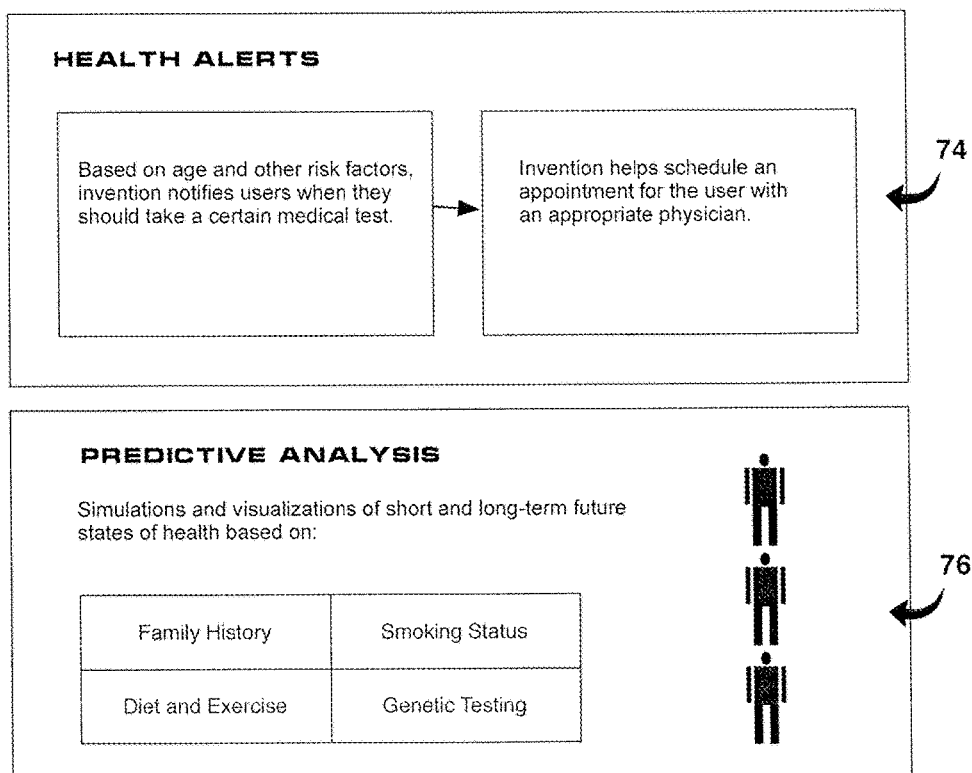
FIG. 9 is a chart representing the future-oriented portion of the timeline functionality of FIG. 7.

FIG. 9 is a representation of the future-oriented portion of the timeline functionality. The timeline may display content regarding a user's future ages to provide future health management. Future health management has two main components: 1) health maintenance alerts (HMAs) 74, and 2) predictive analysis of possible future conditions 76.

The first component, Health Maintenance Alerts (HMAs) 74, refers to user alerts for specific tests and vaccinations based on age, gender, health topics of interest and data inputted by the user or a third party. There are existing standards of care in the medical field that recommend certain tests be conducted at specific intervals or ages, including, but not limited to, colonoscopies, mammograms, and tetanus shots. The application of the present invention identifies users who match these standards based on the users' demographics and other available data in the hospital database. The application alerts the user of upcoming or pending vaccinations, immunizations or tests through the application's in-box. A number appears on an in-box icon, such as on the top right corner of the icon, indicating the number of messages requiring review. Once the user clicks on the icon, he or she is directed to a screen that contains these alerts.

The alert message is generated in such a way to link directly to the hospital services that may be able to fulfill the alert's requirements. All links are managed by the hospital's content management system such that they are appropriate for the types of immunizations or procedures in the alert messages. For example, if a colonoscopy is due for a male turning 50, the alert message contains a link to the hospital's GI service. Once the user clicks on the link, he or she is able to schedule an appointment with a physician who can perform the colonoscopy procedure.

The second component, predictive analysis 76, creates short and long-term visualizations of future health conditions depending on current patient criteria, such as diet, exercise, smoking, family history, and genetic testing. Specific medical standards of care may predict that certain patient habits concerning diet and exercise, and the use of substances such as alcohol and cigarettes, could result in specific diseases or conditions. These standards of care are referenced directly via the application of the present invention. Standard regression analysis techniques are used to identify factors that may predict certain health outcomes. Calculations are based on past data trends of the user as well as sample data from similar patient populations. The application also provides an immediate visualization of possible physical effects due to smoking or increases in weight due to poor diet or exercise. For example, pictures of the user's face are manipulated using standard digital airbrushing techniques to emphasize wrinkles caused by smoking. Likewise, fatty tissue around the cheeks and neck can be added to the user's face to simulate potential weight gain. Morph targets on the 3-D anatomical models are manipulated to show changes in the body, such as increased (or decreased) mass. The user may select individual risk factors from within the "Predictive Analysis" screen, which is accessible via an icon on the application display. Within this screen, the patient may input risk factors, such as but not limited to the average number of cigarettes smoked per day and daily caloric intake. This data regarding a risk factor, along with the age of the patient, allows the application to determine the impact of the risk factor based on current health impact standards. The user then sees a visual display of the medical avatar at time intervals appropriate to the inputs, risk factor, age, and the standard of care. The time intervals could be in days, months or years, and as the user scrolls along these intervals on the timeline, the progression of the illness can be visualized over time as changes occurring to the appearance of the medical avatar. This allows patients to see directly the impact of current habits on their future bodies, and to alter behavior as necessary.

As a use-case example, if a user's tetanus immunization is about to expire or the user is close to the age of 50 and needs a colonoscopy, a health alert appears in his or her in-box indicating this information. The user may schedule each of these health procedures directly through the application, as linkages with local clinicians and hospitals are already present.

In addition, based on current risk factors such as long-term smoking, a 48-year-old user can see how his or her face, lungs and other areas of his or her body are impacted. The visualization is developed using the progression of disease from current standards of care that may be referenced. Once the user selects "smoking" as a risk factor, based on his or her current age and volume of cigarettes smoked, the medical avatar adjusts to reflect the visual profile at time intervals appropriate to the standard of care.

Time intervals may also be adjusted by the user. In the case of the "smoking" risk factor, it may be another 15 years before the lungs are dramatically affected, and the user can see in yearly time intervals the progression of the illness over time.

This type of analysis can be conducted for risk factors that have discrete medical criteria and standards of care associated with them to allow for such a calculation of progression to be made.

Figure 10:
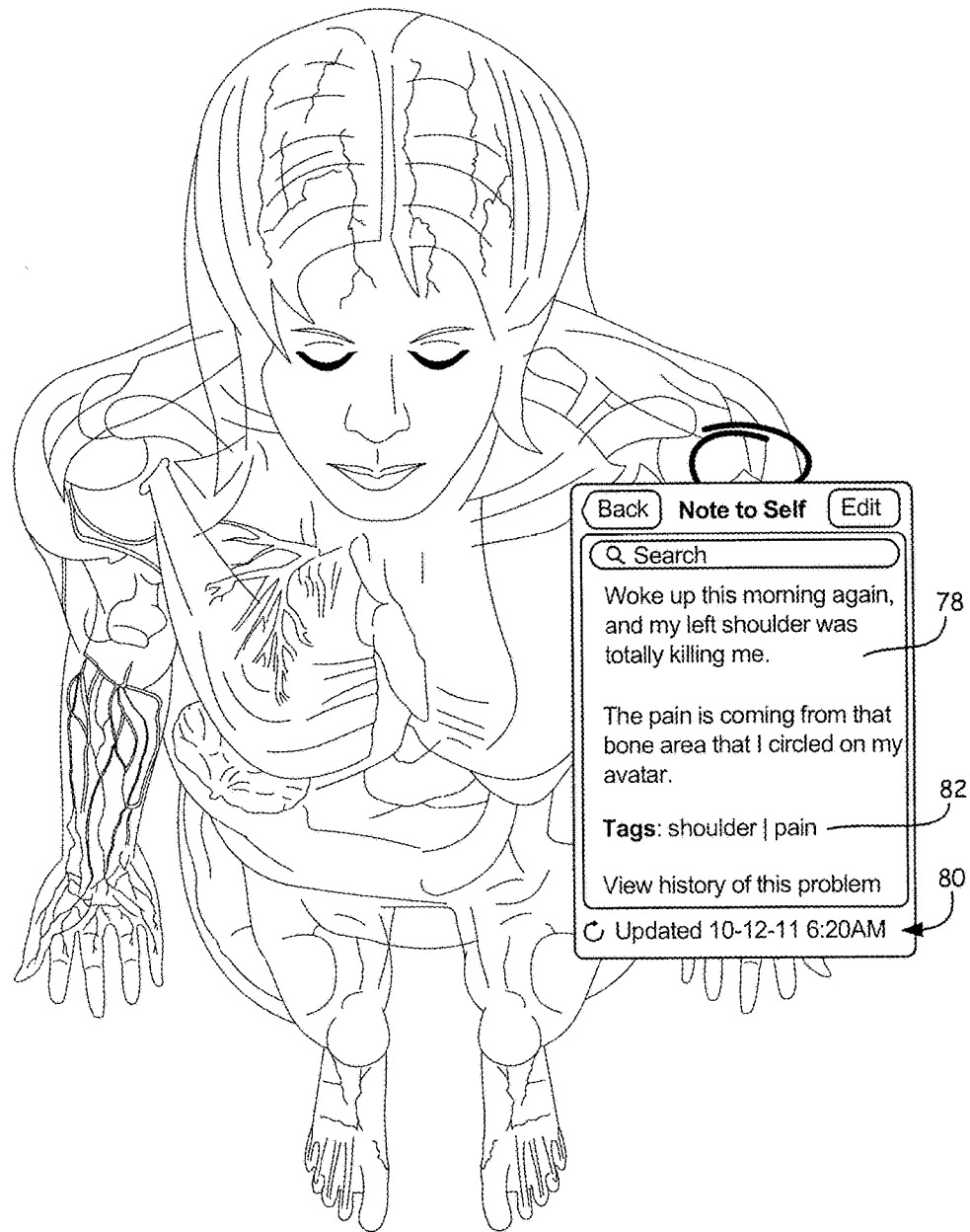
FIG. 10 is a screenshot illustrating the "Note to Self" feature of a medical avatar application.

The application of the present invention may include a "Note to Self" functionality, which allows users to highlight parts of their medical avatars and record corresponding symptoms. FIG. 10 shows a display illustrating the "Note to Self" feature. The "Note to Self" functionality has two main components: 1) tap and press capability that allows a user to add a note 78 to a specific part of the body, and 2) export capability of all or certain filtered notes to standard, compatible file formats.

The first component, which allows a user to interact with the rendered 3-D polygonal body, requires a software development kit (SDK) for the smartphone or tablet computer so the display is configured to allow the user to "tap and hold" a part of the mobile device, causing a blank note, which is very similar to a Post-It® note, to appear. The device keyboard is activated at the same time to allow the user to type a certain number of characters, such as 140 characters, explaining the symptoms of the condition he or she is experiencing. In some embodiments, there is no limit in the number of characters which may be typed. Once the user has successfully input his or her notation and selected "Done," the date and time 80 are automatically captured and a symbol such as an asterisk indicates that a note 78 is present. Regardless of how much the user zooms in or out of the various body layers, the symbol remains to indicate the presence of a note for that specific date and time. If a user scrolls to another date using the timeline, the symbol no longer appears, but the note 78 may be accessed via the "Notes" icon on the display.

To use the "Note to Self" function, the user "taps and holds" an area on the device, which allows the user to manually circle the area in question. In some embodiments, a cursor may be moved using a mouse of a computer in order to circle the desired area. Once the blank note appears, the user may type the symptoms and label the note with a "tag" indicating the location as perceived by the user, such as, for example, shoulder, eye, hip, etc. The user may go back to this tag and produce additional notes under the same tag, creating a group of notes with a common tagged association that the user may refer to at a later time.

Notes are stored in a secure database or on the device itself, accessible in the future using the "Notes" icon on the display. The "Notes" icon contains functionality that allows a user to filter for notes by a tag 82 or even a specific time period. All notes, filtered or otherwise, may be exported to most standard file formats such as .csv, .xls, .doc and .xml. Contained within each export will be the tag 82, date and time 80, and text of the note 78. The user may then organize and analyze this data as he or she deems necessary. The .xml file format also allows for direct HL7-based integration to a portion of the electronic medical record (EMR) to allow the medical care provider to review such notes prior to seeing the patient.

As a use-case example, if a user suffers cramping near the right hip, the user may motion towards the right hip region on the Medical Avatar, zoom in to see the musculoskeletal layer and "tap and hold" to add a 140 character note regarding the cramping. The user may tag the note as "hip" or "right hip" or "right hip pain," depending on how specifically the user wants to indicate the problem.

This note is recorded with an associated timestamp to approximate the time and date when the symptom was present. If the user re-experiences this pain, but in a region slightly left of where he or she originally experienced it, he or she may once again zoom in, locate either the original tag that most closely matches the location of the pain, and document another 140 character note. The user can continue to do this for the same set of tags depending on the frequency of the pain. Over an extended period of time, exact timestamps with noted details will serve as a future reference for the user and clinician.

If the user has an appointment with an orthopedist, for example, to diagnose the pain, he or she may use the app to concisely share his or her medical narrative. The physician is better able to make an accurate diagnosis as he or she has full access to symptoms and other details that may be difficult to communicate verbally. The patient can also export a part or all of the notes he or she has entered about the symptoms into a compatible file format to share with the doctor. The file may be downloaded and printed, shared via email, or even shared via a direct interface to the doctor's EMR system. In this case, the problem may range from being a hernia in the abdominal region or a sprain of the hip, but exact notations of the symptoms add to the volume of evidence and exact testimony to make such a diagnosis.

The notes are perpetually available for a specific user's profile. If, two years down the line, the user begins to once again experience a similar pain, he or she may refer back to the previous notes to determine similarities or differences. Serving as a journal-like repository of symptomatic inputs, this "Note to Self" function allows both a user and a physician to track the symptoms of an illness over time, thereby facilitating diagnosis and treatment.

Figure 11:
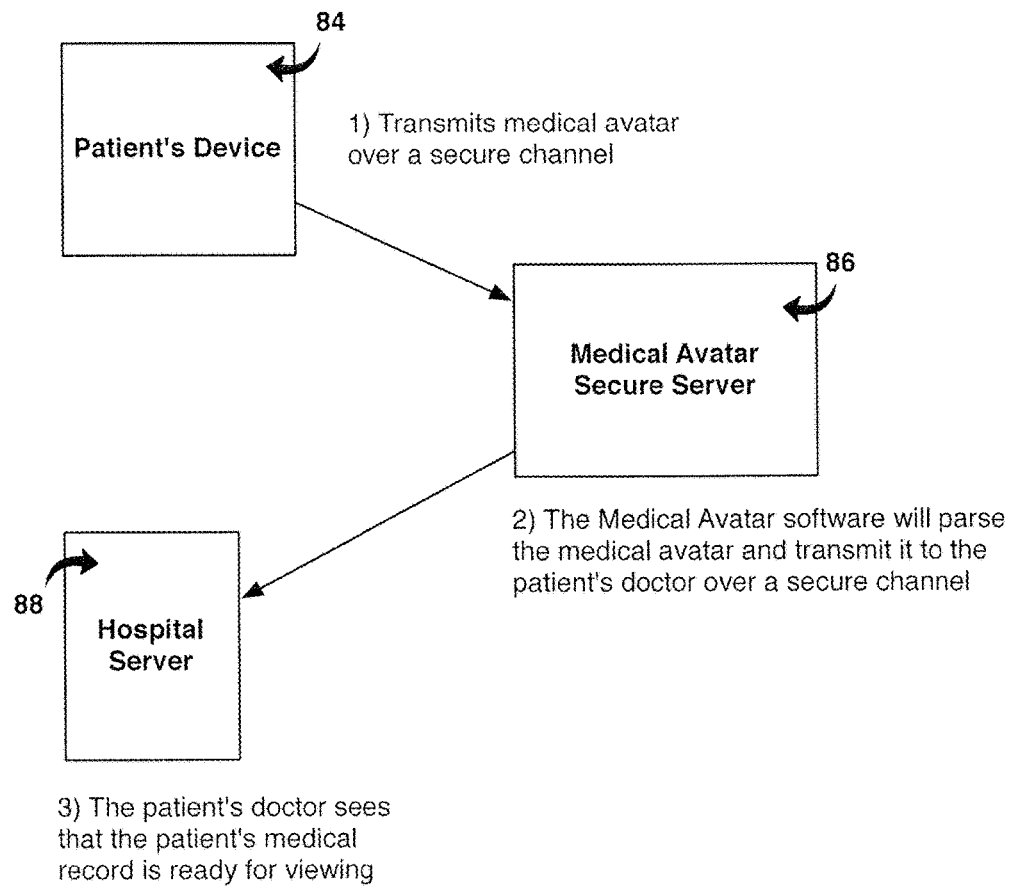
FIG. 11 is a chart representing the data sharing functionality of a medical avatar application.

The application of the present invention may include a data sharing functionality, which allows data to be shared between a user and a designated clinician. FIG. 11 is a chart representing the data sharing functionality. The data sharing functionality has two main components: 1) full transfer of data over secure servers, and 2) limited transfer of data over social media.

The first component, full transfer of data, facilitates the ability to send data from a user's device 84—smartphone, tablet, laptop, or desktop—across a secure third party server 86 directly to a verified clinical provider. The user's device 84 stores the most recent and updated version of his or her medical avatar. When the user chooses to share the medical avatar with his or her clinical provider, the user can tap and select a "share" button on the display. A list of providers appears with whom the user may share data. The user can decide who to send the data to depending on the medical specialty of the provider, such as primary care, orthopedics, nephrology, etc.

Once a clinical specialist is chosen, the user has the option of limiting the data that will be sent by tapping on the "Filter" icon to filter for the various elements within the medical avatar, such as but not limited to conditions, medications, laboratory results, and notes. The user may also filter for specific time periods in the timeline by selecting a start and end date. If the user wants to send all current medical information associated with the medical avatar, he or she does not need to filter the data and may simply select "Send."

In one embodiment, the data is packaged in JSON files and sent in real-time through a secure channel to a secure third party hosted server 86. The package is parsed via a JSON parser for the hospital and clinical provider to whom it is being sent. The parsing of the data depends on the content management system or the electronic medical record system to which the data is being sent. Parsing of the data may occur very quickly, in a matter of seconds, and the data is sent to the hospital's server 88 across a secure channel.

Once the packaged and parsed data is received by the hospital server 88, it is redirected to the appropriate clinical provider. The data can appear in various formats, within the hospital content management system's console, the electronic medical record's updates, or through the clinical provider's medical avatar. An alert appears indicating data has been received and requires further review.

The second component of data sharing, limited social media transfer, allows users to share their data over multiple social media platforms such as, but not limited to, Facebook, Twitter, and Google+. Due to the limitations of display on the various social media platforms, the application generates a formatted view of the information to be displayed. The limited format begins with the personalized anatomy of the user. In one embodiment, the user then has the option to share a two-dimensional JPEG picture or text depending on the elements of the medical avatar they'd like to share. The user can select from other display components such as the labels of the diseases, conditions, medications and notes, and the timeline of the medical avatar the user wants to share, such as past, present or future medical avatars. The user may choose to send his or her selection to multiple social media platforms at once. Once the user has made the selection, the picture or text is sent to the selected social media and displayed in the associated format.

Figure 12:
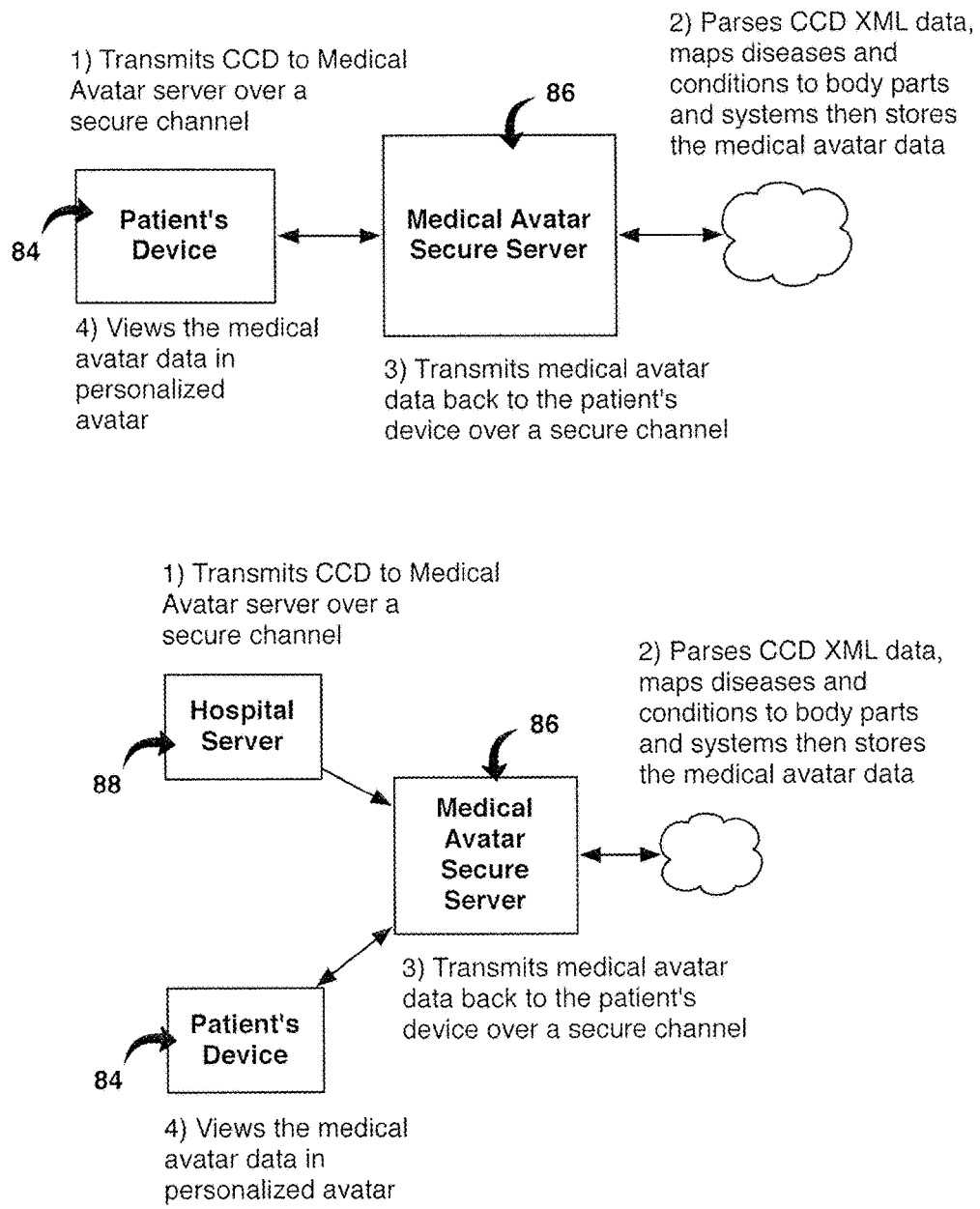
FIG. 12 is a chart representing the Continuity of Care Document (CCD) Viewer functionality of a medical avatar application.

The application of the present invention may include a Continuity of Care Document (CCD) Viewer functionality, as represented in the chart shown in FIG. 12. The Continuity of Care Document Viewer or "CCD Viewer" has two main components: 1) export from hospital, and 2) anatomical mapping to the medical avatar.

The CCD is an XML-based, government-approved standard that aggregates various elements of a patient's record in a summary meant to facilitate clinical exchange of information. It consists of the following 17 elements: header, purpose, problems, procedures, family history, social history, payers, advance directives, allergies/alerts, medications, immunizations, medical equipment, vital signs, functional status, results, encounters, and plan of care. As of the publication of the American Recovery and Reinvestment Act in 2009, hospitals and individual clinical providers are required to provide a clinical summary to their patients. This may be in the form of a PDF document or an XML document in the CCD standard. Electronic medical records (EMRs) have the ability to generate both.

The purpose of the CCD Viewer is to leverage the output of the EMR and create a visual, user-friendly dashboard for users on a mobile platform. First, a secure export of the CCD data is required. In its simplest form, a CCD can be exported from the hospital or clinical provider's EMR and given to the patient in a compact disc (CD) or other physical medium, or sent over a secure channel to the patient's personal health record (PHR). The latter allows for a seamless transfer of CCD information from the EMR to the PHR. Whether via the compact disc or the PHR, the user may download the CCD to his or her device 84, such as a personal computer, smartphone, or tablet, via an in-app browser that navigates the user to the appropriate web page utilized by his or her clinical provider to share protected health information. Data can also be accessed using the in-app browser to access the user's email account to pull the appropriate file. The user may also use iTunes sync functionality from his or her device to upload the appropriate information. Once the CCD is downloaded to the device, the user may login to the application, select the import icon, and choose "CCD" from the option menu. The application will then search for ".xml" files within the user's device. Once the search is complete, the user selects the appropriate file and the application imports the CCD data directly to its anatomical interface.

Second, the CCD data is mapped to the application's CCD Viewer dashboard. Certain elements of the CCD are not anatomical and therefore the data must be parsed into two distinct categories: anatomical and non-anatomical. Anatomical elements are problems, procedures, family history, allergies/alerts, vital signs, and results. Non-anatomical elements are the header, purpose, social history, payers, advance directives, medications, immunizations, medical equipment, functional status, encounters, and plan of care. Anatomical elements have detailed data that relate directly to the anatomy of the patient's body. An association may be made between each anatomical data element and the patient's anatomy.

Based on ICD codes (International Statistical Classification of Diseases and Related Health Problems), any injury, disease, and condition—including signs, symptoms, abnormal findings, complaints, social circumstances, and external causes of injury or disease—are mapped to specific anatomical objects in the medical avatar. Every anatomical object in the 3-D models is named based on standard terms in the Metathesaurus of Unified Medical Language System (UMLS). The software uses UMLS controlled vocabularies and classification systems to connect ICD codes to the corresponding anatomical part.

The non-anatomical elements are organized in a dashboard within the application with their associated data reformatted to suit the application's interface. The user selects the dashboard menu and a dropdown menu appears with a list of the non-anatomical elements that were imported from the CCD. The user may select "Medications," for example, to display the list of medications noted within the CCD. The information may appear in the font and design of the application. Similarly, the user may select any of the other non-anatomical elements to display the detail.

An upload of a CCD on a particular date represents a snapshot in time of the patient record. Any and all information recorded within is relevant up to the date the CCD was recorded and uploaded in the form of a medical avatar. Any symptoms, issues, problems or diagnoses occurring after the upload of the CCD and recorded separately from inputs in the medical avatar will not be part of the original CCD. Once another CCD is requested from a clinician at a future date, any information added since the original upload of the CCD will be present in the new snapshot. For example, if a CCD is requested and uploaded in May of 2007, it represents information in a user's record up to that point. If the user goes to a clinician suffering from a headache, sore throat and fever after the upload of the CCD in May, 2007, another CCD must be requested at that date or a later date from the clinician to ensure the data is recorded. This limitation is due to the structure of the CCD, not the application. Multiple CCDs inputted in the format of the application provide a long-term tracking view of trends and changes in the clinical history of the patient.

As an example of the use of a CCD, a user may go to see his or her nephrologist for end-stage renal disease (ESRD). After the visit, the user requests a clinical summary in the format of a CCD. The staff at the nephrologist's office either exports the CCD data onto a compact disc or other physical medium, or directly to the patient's PHR.

The patient logs in to the medical avatar application and taps on the "Import" icon and selects "CCD" from the menu options. The patient sees a list of .xml files and selects the appropriate file. The data from the file maps both anatomical and non-anatomical elements onto the CCD Viewer dashboard. The user may then use the dashboard to view non-anatomical elements, such as medications and plan of care, or to select anatomical elements, such as problems and vital signs which are displayed directly onto the anatomy of the personalized medical avatar.

Figure 13:
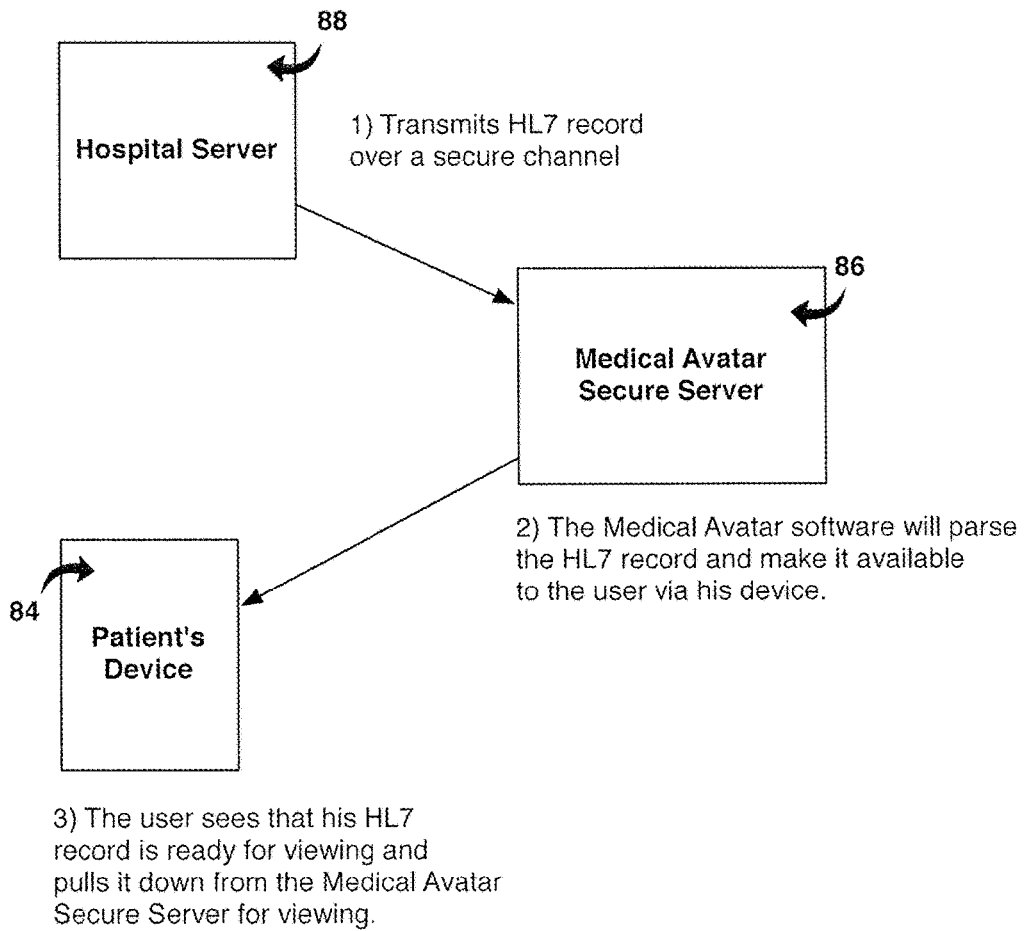
FIG. 13 is a chart representing Health Level 7 (HL7) import functionality of a medical avatar application.

The application of the present invention may include a Health Level 7 (HL7) import functionality, which allows data to be imported in HL7 format. FIG. 13 is a chart representing the HL7 import functionality. HL7 import contains one primary functionality: the anatomical and non-anatomical mapping of medical information within an electronic medical record directly to the application interface.

Health Level 7 refers both to the organization that creates the medical standard and the medical standard itself. The standards generated by HL7 create a structure for interoperability between various software systems. There are HL7 standards for messaging, clinical decisions, medical conditions, visual integration, billing claims, document architecture, medications, and electronic and personal health records.

Similar to the algorithmic mapping of CCD data, the medical avatar application maps HL7 data in both anatomical and non-anatomical formats. The HL7-to-anatomy mapping is done either by an accredited clinical provider or a medical informaticist. Each HL7 standard is first determined to be either anatomical or non-anatomical. Next, the non-anatomical elements are re-formatted to match the font and design formats of the application. The non-anatomical elements are then arranged in a standard dashboard listing to be selected by the end-user.

Mapping of the anatomical elements depends on the language and format of the HL7 standard, such as SAIF, Arden, MLLP, CCOW, etc. Each anatomically-related language or format is parsed and mapped to the patient anatomy to display onto the personalized medical avatar.

The application plugs directly into the hospital or clinical provider's HL7 standards. Once both anatomical and non-anatomical mappings are complete, the user can view the entirety of medical information within the application's visual framework. The transfer occurs by securely transmitting the HL7 record directly to the application's secure server where the information is parsed. Both anatomical and non-anatomical elements are then mapped directly to the application to appear on the user's device 84, whether personal computer, smartphone or tablet.

Figure 14:
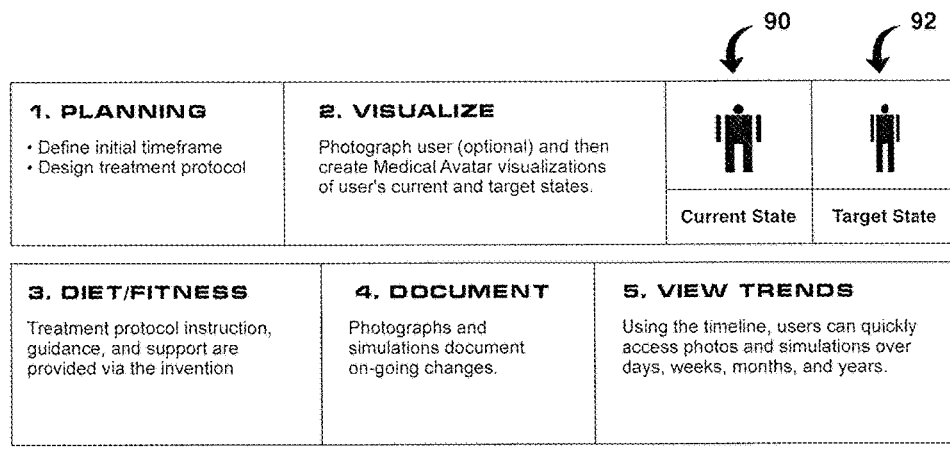
FIG. 14 is a chart representing the weight loss visualization functionality of a medical avatar application.

The application of the present invention may include a weight loss visualization functionality, to facilitate a user's weight management. FIG. 14 is a chart representing the weight loss visualization functionality. Weight loss visualization has three main components: 1) current and target comparison states, 2) treatment protocol instruction, and 3) documentation of progress.

Weight loss visualization begins with defining current and target states. The user logs into the application, selects "weight-loss visualization" from the options menu and is immediately taken to a profile screen to define the "Current" state 90. A user's current weight, height and body mass index are necessary metrics to be input into the application if they are not already present. The user may use the last documented metrics from a medical record or previous recording by selecting "use prior metrics." This selection will populate each field with the necessary information by accessing the data from the most recent match to the requested field. The user may also enter measurements such as waist, chest, and neck sizes—or specific clothing sizes—to define bodily dimensions for current and target states.

In one embodiment, to further enhance the visualization and provide an actual view of the user, a full-body picture of the user in the current state may be embedded directly into the application. After inputting initial metrics and selecting "Next" on the screen, the user is taken to a "Picture" screen where the user may select "Choose picture" for an existing, recent picture, or "Take picture" to take a new picture. Once the user has done so, the picture is mapped to the medical avatar within the application. The user also has a third option to not take a picture and instead select "Choose body shape." This allows the user to select from various body morphs to define exactly what kind of body shape the user currently has. Once the user selects "Choose body shape," he or she is directed to another screen with options such as "mesomorph," "ectomorph," "endomorph," or a "combination of body shapes." The user selects the morph that most closely matches his or her current body shape. Once complete, the medical avatar adjusts graphically to incorporate height, weight, and BMI metrics along with the body shape to render a more exact "Current" state 3-D animation of the user. Details of body personalization were provided above. If satisfied with the body shape provided, the user may select "Next" to continue.

The user's "Target" state 92 must now be defined. In the first stage of the "Target" state section, the user is directed to a visual rendering of his or her current morph state and can use his or her thumb and forefinger to shrink or expand the width of the user. If the user is using a computer, the user may alternatively use a cursor and mouse to shrink or expand the width of the user. As the user applies this motion to the device and application, a weight meter field to one side of the animation indicates the amount of weight reduction within recommended guidelines. Constraints are established based upon recommended BMI, i.e. 20-25 for optimal weight. Also, a time meter field just below the weight meter field shows the approximate number of months required to reduce weight to the target level. The computation of time is directly linked to FDA-approved treatment protocols. For example, if the user's "Current" weight is 230 lbs, and he or she shrinks the current state of his or her Medical Avatar to 180 lbs, the reduction of 50 lbs may indicate a range of 10-16 months in the time meter field, deemed appropriate by FDA regulations. Once the user has decided on the "Target" state 92, he or she may continue by selecting "Next."

The second component of weight loss visualization is treatment protocol instruction. Based on the user's selection of "Current" and "Target" states 90, 92, there are a limited number of FDA-approved treatment protocols for weight loss recommended for the user. In the "Treatment Protocol" section, the user goes through the process of selecting the most appropriate treatment protocol depending on his or her dietary restrictions, daily schedule, current eating habits, nutritionist counseling, and any other variable that may guide his or her selection. In one embodiment, three treatment protocols are provided: "Treatment Protocol A," a more rigorous approach to diet that in the previous example would indicate a weight loss goal of 5 lbs/month; "Treatment Protocol B," a moderate approach to diet that in the previous example would indicate a weight loss goal of 4 lbs/month; and "Treatment Protocol C," a simpler approach to diet that in the previous example would indicate a weight-loss goal of 3 lbs/month. Once the user makes his or her selection, the user may continue by selecting "Next."

The third component of weight loss visualization is documentation of progress. Based on his or her selection, the user is provided a checklist of FDA-approved instructions for his or her weight-loss goal. Each element of these instructions has stages where the user may document his or her progress, by undergoing the same process of selecting the body shape as he or she did in the "Current" state 90. For example, if the user selects "Treatment Protocol B," the moderate approach to weight-loss, he or she may be provided a 5-step plan for reducing his or her weight an approximate 4 lbs/month. As users go through each step of the plan, they may document pictorially their progress at each step. Additionally, monthly markers create additional motivation markers. From the start of the weight loss visualization, every month the users are asked to once again go through the body shape selection process as they did in the "Current" state 90. They may embed pictures of themselves or simply select the morph that best suits their body shape at that point in time. However, users may add pictures at any point and are not restricted to only the monthly or step markers. These are simply default markers that alert the user throughout their dietary initiative to document their progress on a regular basis.

Users may use the application timeline at any point of the weight loss visualization to review their progress. Scrolling from right to left on the timeline allows the user to review notes, pictures, and milestones of the treatment protocol. The user or a clinical provider may make any adjustments to the treatment protocol based on this review.

Figure 15:
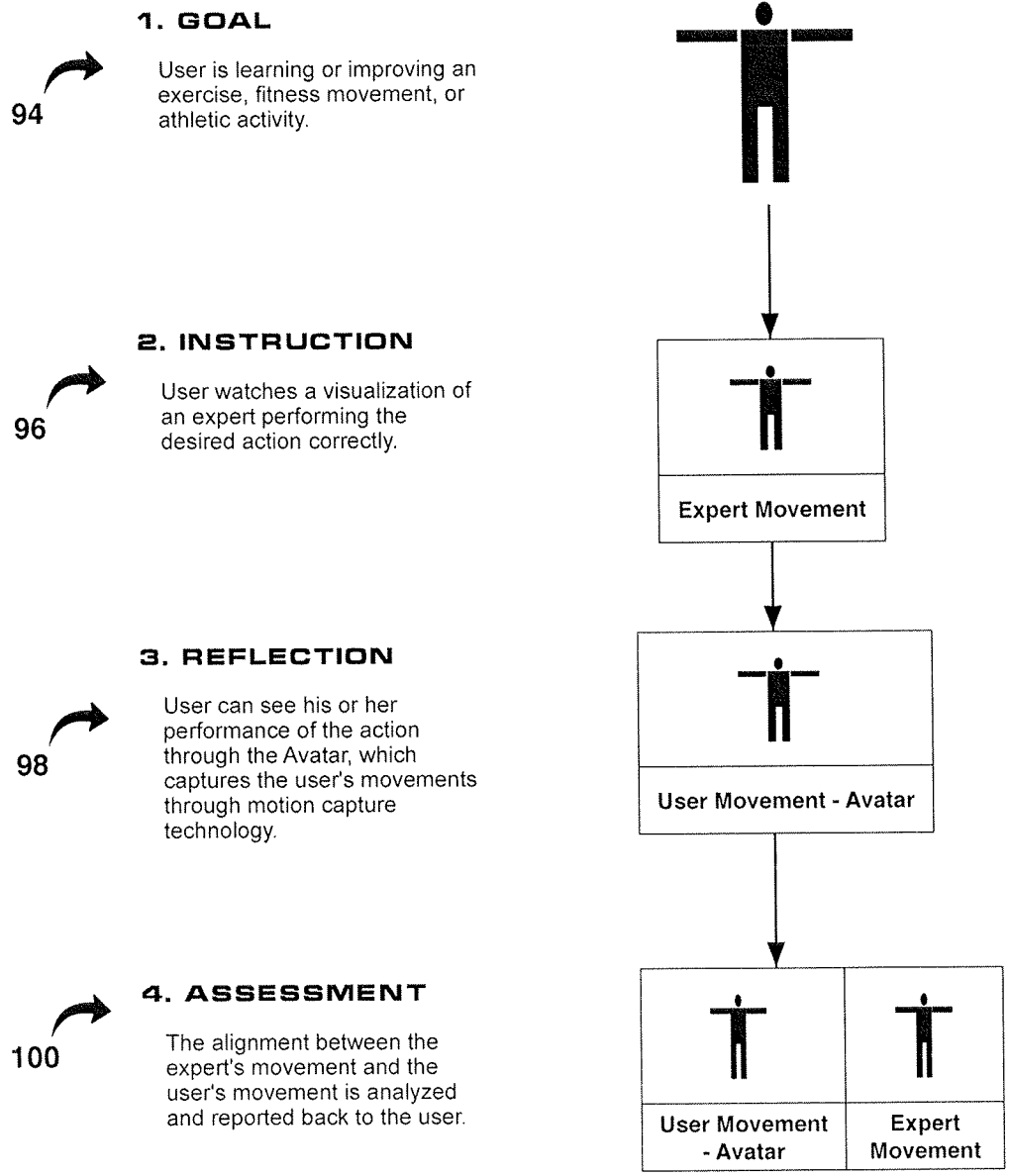
FIG. 15 is a chart representing the fitness training visualization functionality of a medical avatar application.

The application of the present invention may include a fitness training visualization functionality, to facilitate a user's exercise, fitness, and athletic training. FIG. 15 is a chart representing the fitness training visualization functionality. Fitness training visualization has four main components: 1) fitness goal selection 94, 2) expert technique instruction 96, 3) user reflection 98, and 4) comparison assessment 100.

The first component, fitness goal selection 94, starts with the user's exercise, fitness or athletic goal. Data from health mobile devices, including FitBit and Body Media, that record user fitness statistics may be imported into the application. Numerous movement activities may be taught through the application, including but not limited to sports such as baseball, basketball, football, and golf. A user may, for example, select baseball and choose to enhance his or her baseball pitch or baseball bat swing. A user may select basketball and choose free throw, jump shot or dribbling; select football and choose a spiral or slant route; select golf and choose driving, putting or chipping; and so on. The user may also select from a range of fitness activities such as, but not limited to, calisthenics, body-weight exercises, yoga, and pilates.

Once the user has selected a fitness goal, such as a free throw in basketball, he or she selects "Next" and is taken to a section where he or she may select expert technique instruction 96 based on his or her preference or height/weight restrictions. For example, a 6'2", 210 lb user may choose Stephon Marbury's technique and a 6'8", 260 lb user may choose LeBron James' technique, or the user may simply choose the expert he or she prefers. There are multiple experts in each sport embedded within the application to choose from. Once the user makes a selection, the next screen within the application shows the expert performing the technique. The stance, motion, extension and follow through of a free throw may be displayed in multiple body layers. The default is the external body of the expert performing the free throw, though the user may select the muscular or skeletal layer to view another perspective. The user may rotate or zoom as the expert motion is displayed to better understand the technique being used. Once the user is satisfied, he or she may select "Next" to continue.

A motion capture device such as the Microsoft Kinect is required for the third component of fitness training visualization. User reflection requires the users to mimic the expert technique they just viewed using the motion capture device. The users may imitate the free throw motion multiple times and select the motion they believe matches the expert technique the most. Once they have completed the user reflection 98 on the motion capture device, data regarding the users' movements may be imported within the application.

The users may then utilize the fourth component, comparison assessment 100, to review and compare their reflection of the expert technique with the expert technique itself. Each user's movement, as captured by the motion capture device, is compared with the selected expert movement in real-time. Discrepancies between the user and expert trigger alerts that highlight the offending parts of the body and the exact moments when the movements diverged. An "instant replay" video is filmed to show frame-by-frame comparisons of the movement performed by the user in contrast with the expert. The user can clearly see where his or her motion is different from the expert and make the necessary adjustments. The user is prompted to try again and perfect the movement.

Figure 16:
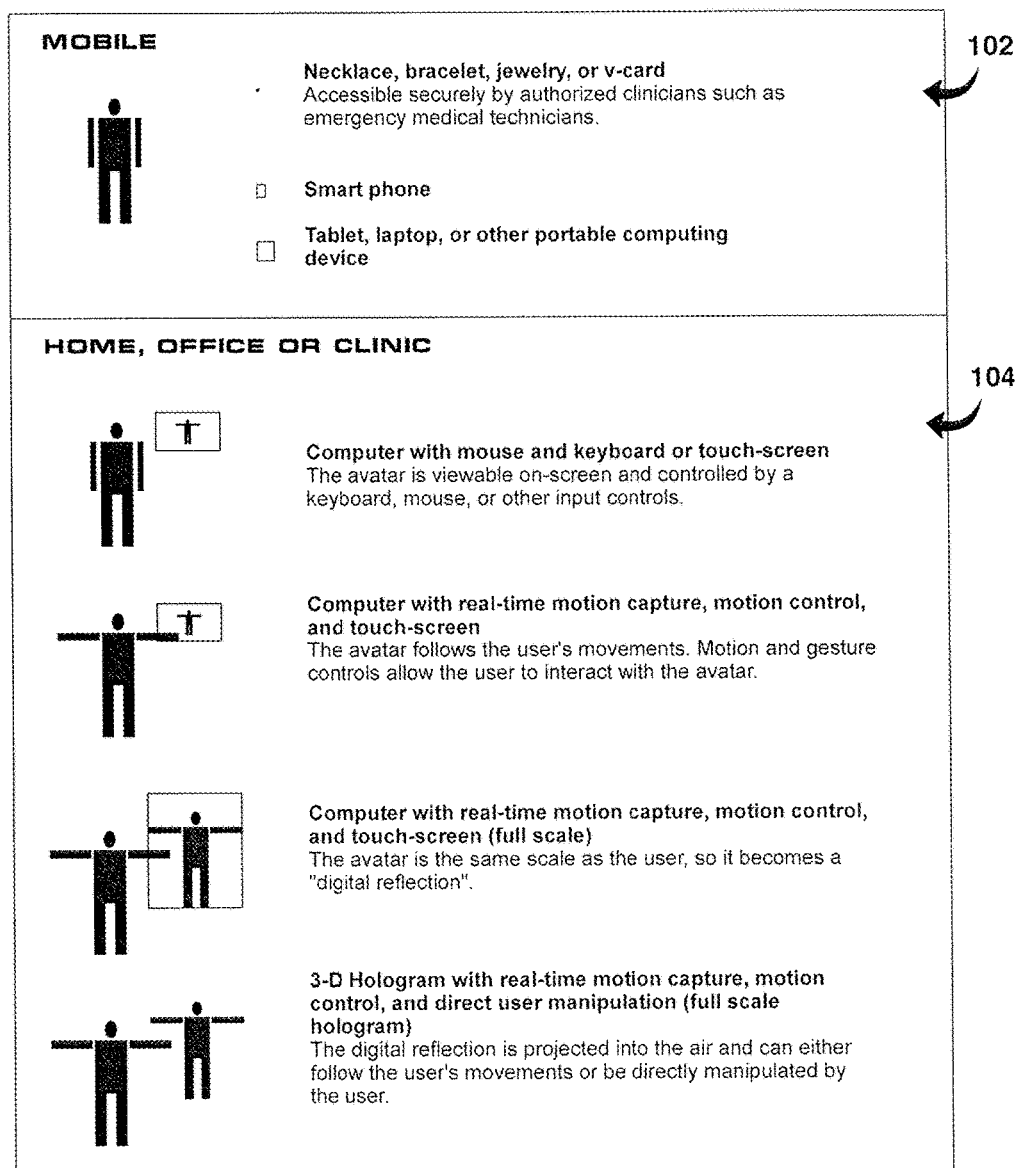
FIG. 16 is a chart representing the interface modalities of a medical avatar application.

Users may access the medical avatar application in a variety of different ways. FIG. 16 is a chart representing the interface modalities. Interface modalities have two main components: 1) secure backup of application data, and 2) interoperable relay to multiple device platforms.

The primary component to interface modalities is secure backup of application data. Regardless of the device used to access the application, user-inputted data is securely archived on a local or third party server. User identifier information is anonymized and only profile information is retained within the server. This allows users to access their information from anywhere on multiple devices. It also allows for authorized, third party users such as clinical providers to access de-identified user information for research and review purposes.

The second component of interface modalities is the ability to make the data interoperable and relay it to multiple device platforms. Mobile device platforms 102 include tablet computing devices (e.g. iPad, Galaxy, Nexus, etc.) and smartphones (e.g. devices running iOS, Android, Windows, etc.). Additional devices 104 include but are not limited to desktop computers (Dell, Apple, IBM, etc.), game systems with real-time motion capture (Microsoft Kinect), wearable technologies (Google Glass), TVs, and holographic display devices that allow a user to project application data in the air or a flat surface. Mobile devices 102 such as jewelry or scannable cards may also serve as repositories of access. Military-style "dog tags" may provide secure access to medical records for military personnel as well as the general public. Scannable cards embedded with quick response (QR) code technology may also be carried with the user on his or her person. This will allow emergency responders to quickly access information in case the user is incapacitated.

Figure 17:
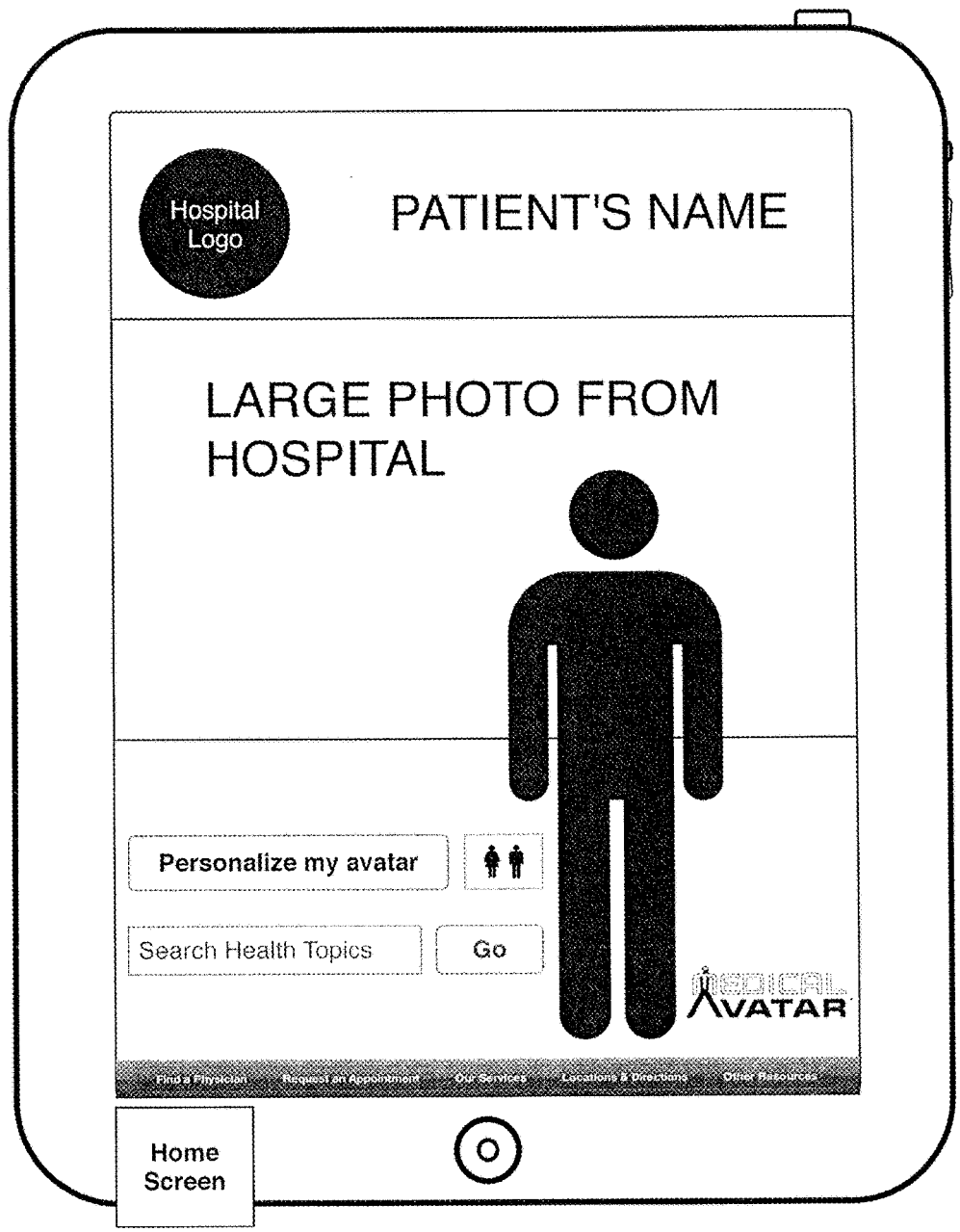
FIG. 17 is a wireframe showing how an embodiment of the present invention may be customized for a specific hospital.
Figure 18:
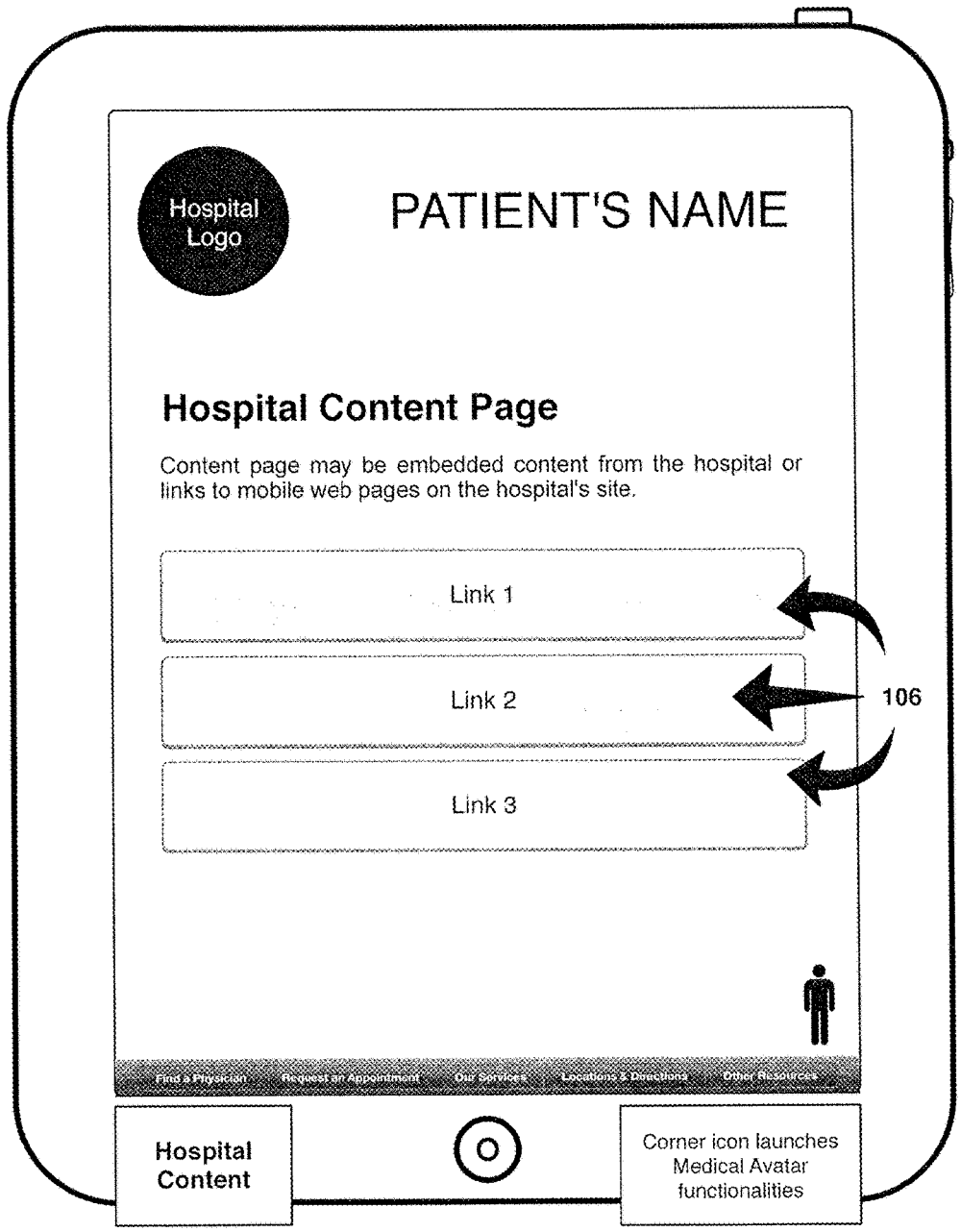
FIG. 18 is a wireframe of the embodiment of FIG. 17, showing a page of the software application which presents links to hospital content.
Figure 19:
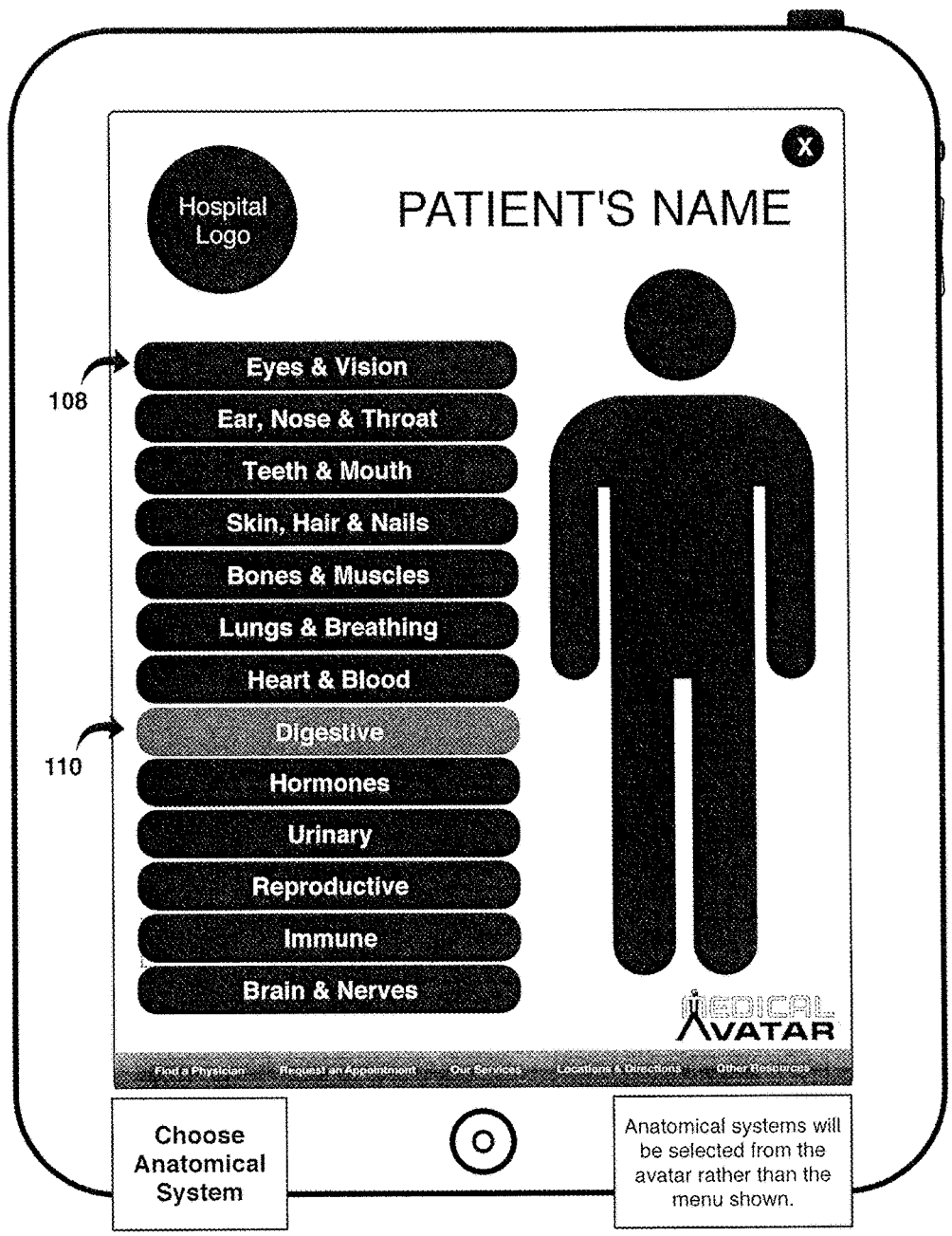
FIG. 19 is a wireframe of the embodiment of FIG. 17, showing a display including a menu listing the anatomical systems.
Figure 20:
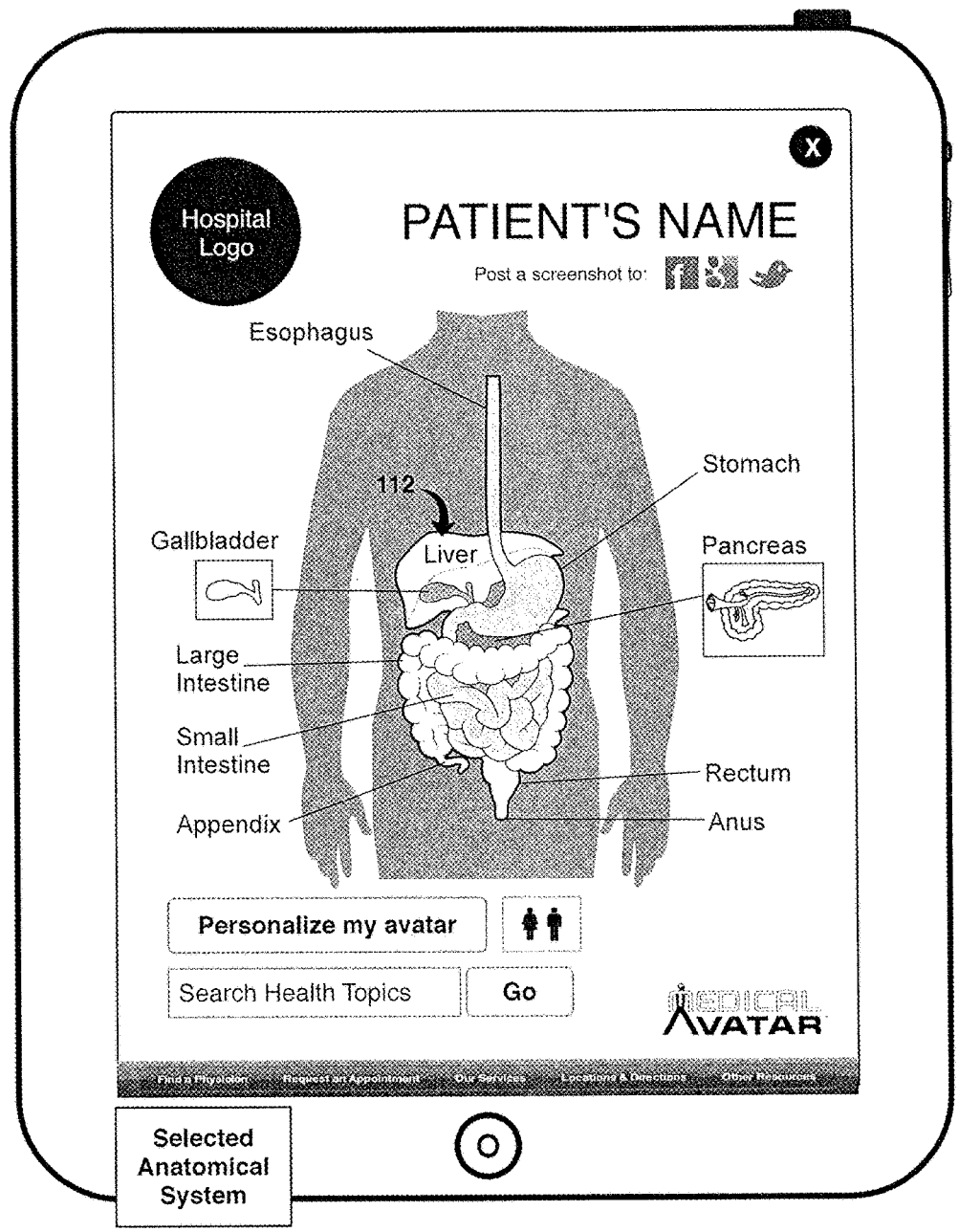
FIG. 20 is a wireframe of the embodiment of FIG. 17, showing a display including a medical avatar comprising organs of a selected anatomical system.
Figure 21:
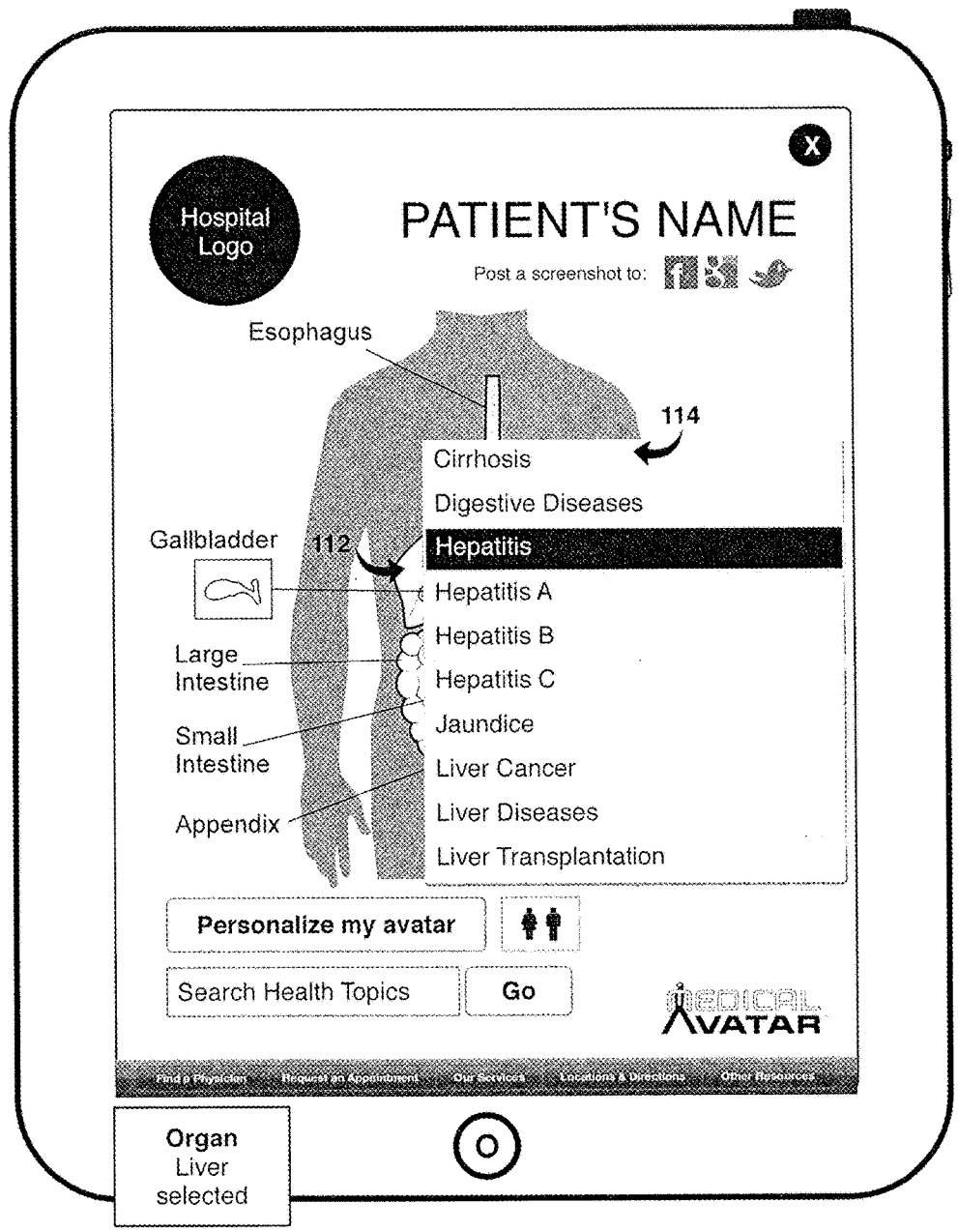
FIG. 21 is a wireframe of the embodiment of FIG. 17, showing a display including a menu listing conditions and diseases associated with a selected organ.
Figure 22:
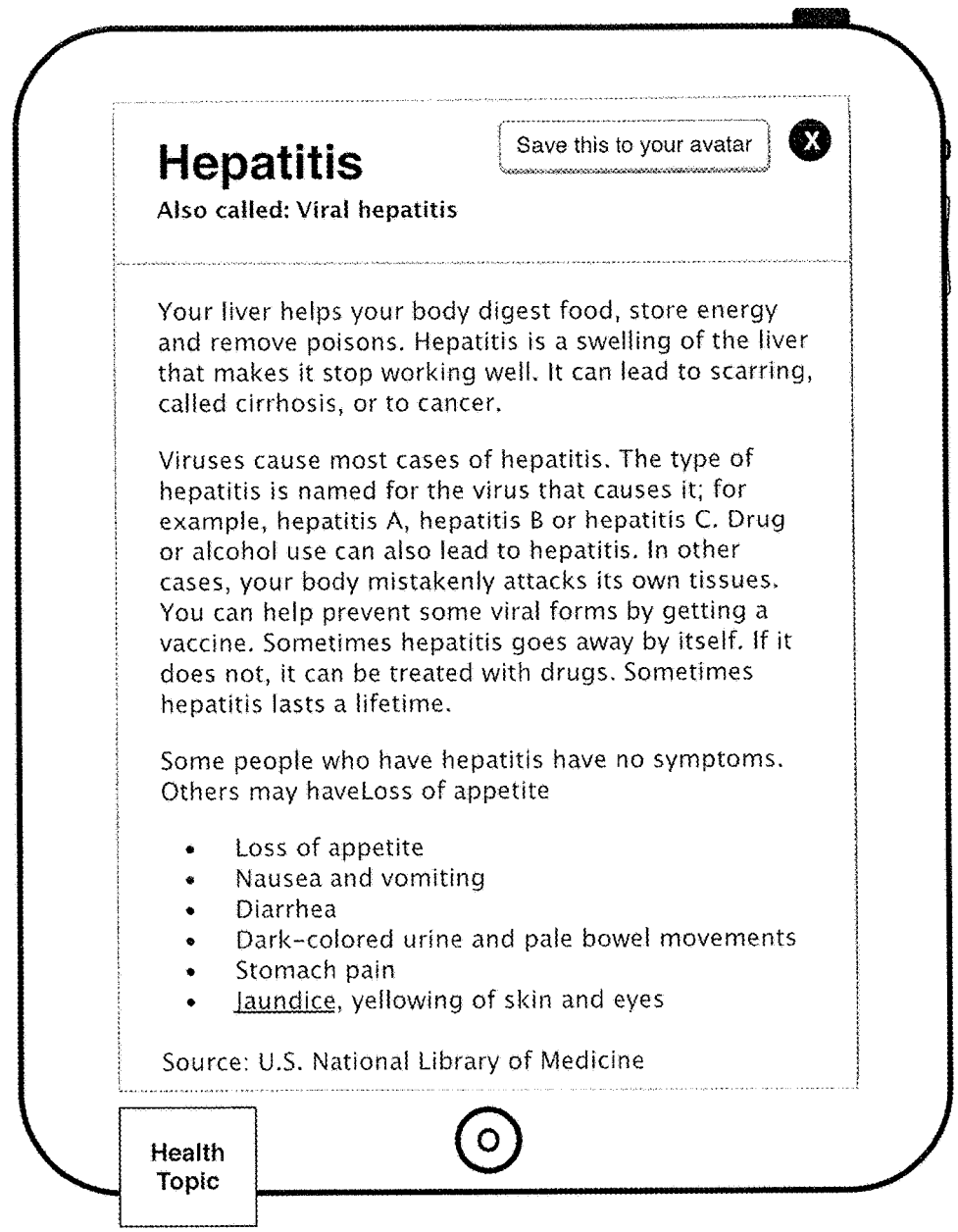
FIG. 22 is a wireframe of the embodiment of FIG. 17, showing a health topic page containing information regarding a selected condition or disease.
Figure 23:
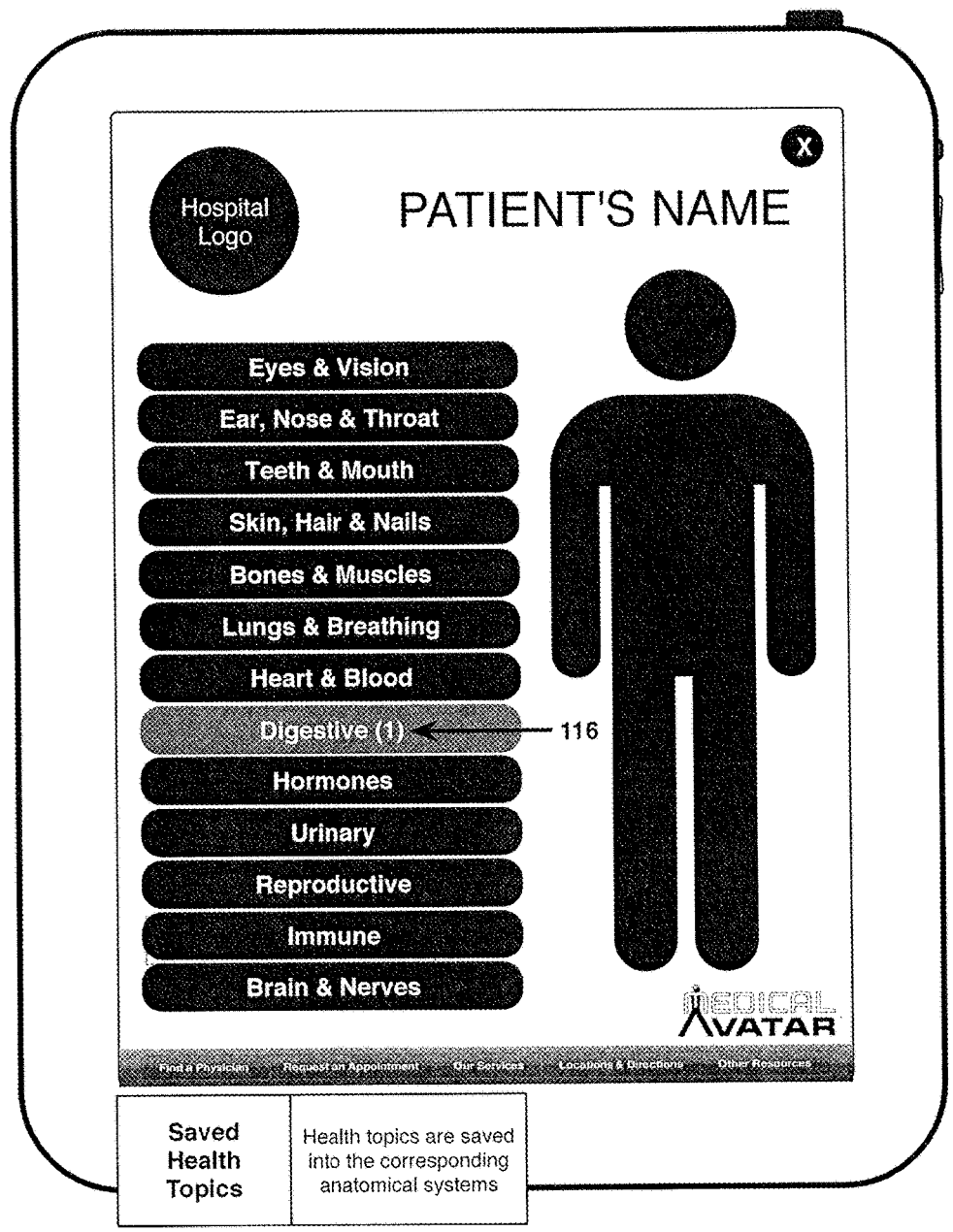
FIG. 23 is a wireframe of the embodiment of FIG. 17, showing a display including a listing of anatomical systems with a saved health topic.
Figure 24:
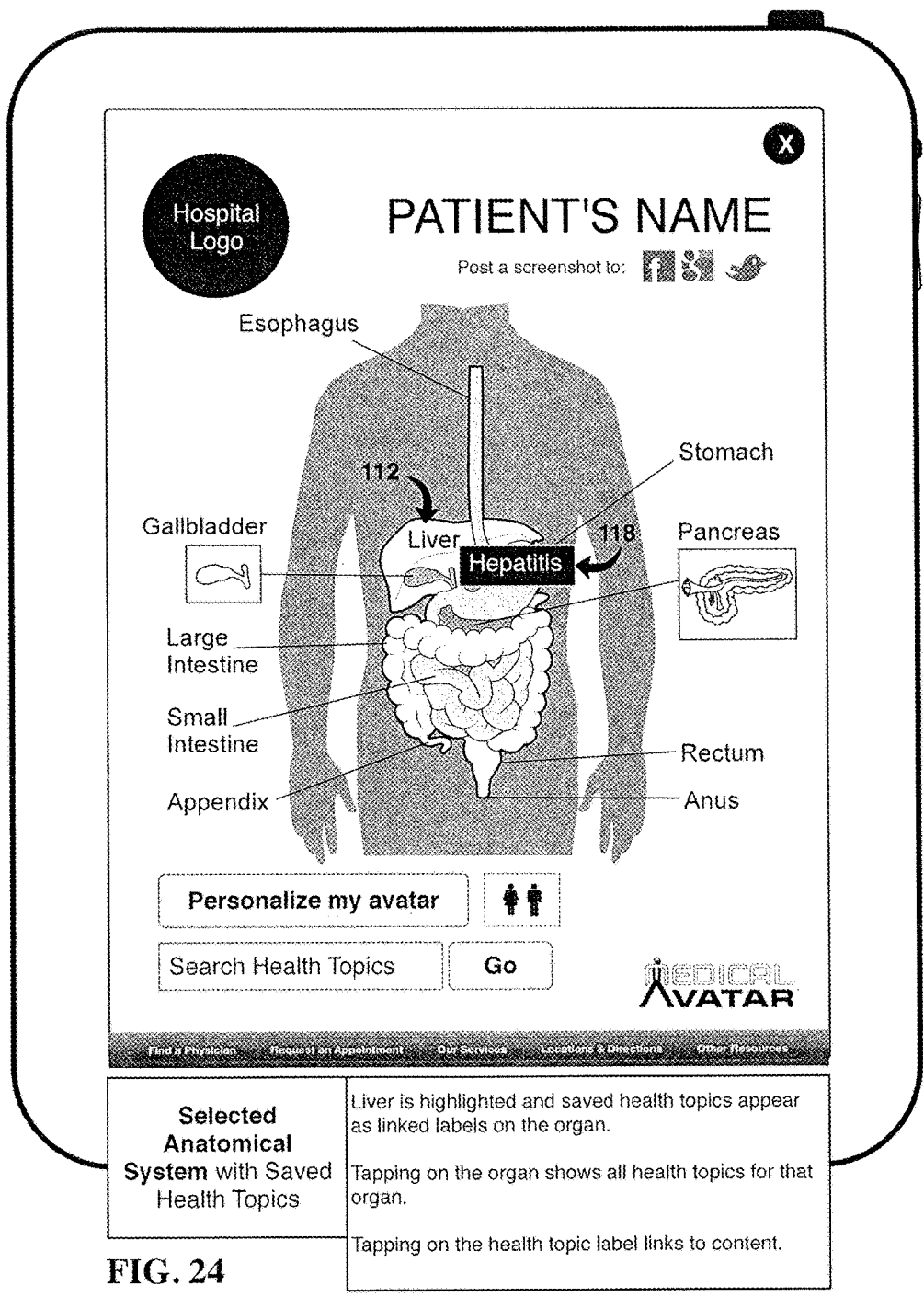
FIG. 24 is a wireframe of the embodiment of FIG. 17, showing a display including a medical avatar comprising organs of a selected anatomical system with a saved health topic.

Wireframes of an embodiment of the medical avatar application of the present invention are shown in FIGS. 17-24. FIG. 17 provides an example of how an application may be customized for a specific hospital. FIG. 18 shows a page of the application which presents links 106 to hospital content. FIG. 19 shows a display including a menu 108 listing the anatomical systems. A wireframe of the display which results when the button 110 labeled "Digestive" is selected from the menu 108 is shown in FIG. 20. A specific organ 112 of an anatomical system may also be selected, as shown in the wireframe of FIG. 21. FIG. 21 also shows that, upon selection of an organ 112, a menu 114 listing conditions and diseases associated with the selected organ may be displayed. Selection of a condition or disease from the menu 114 directs a user to a health topic page containing information regarding the selected condition or disease, as shown in FIG. 22. A health topic may be saved by a user. A saved health topic may be indicated in the listing of anatomical systems by a number 116 following the name of the corresponding anatomical system, as shown in FIG. 23. Saved health topics may also appear as linked labels 118 on the corresponding organ 112 of the medical avatar, as shown in FIG. 24. Tapping or clicking on the organ causes the display to show all health topics for that organ. The health topic labels 118 link to content regarding each health topic.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of presenting health-related information, the method being performed by execution of computer readable program code by at least one processor of at least one computer system, comprising:
   providing, by at least one processor of at least one computer system, a three-dimensional anatomical model of a human, said three-dimensional anatomical model comprising a plurality of anatomical systems, wherein the three-dimensional anatomical model comprises a plurality of polygons;
   receiving, by the at least one processor, physical attributes data of a user, and two photographs of the user from a device's camera;
   creating, by the at least one processor, a personalized anatomical model by altering an appearance of the three-dimensional anatomical model based on the physical attributes data of the user and the two photographs of the user,
   wherein altering the appearance of the three-dimensional anatomical model includes manipulating a morph target of a polygon of the plurality of polygons to change the shape of said polygon based on the physical attributes data including a height, weight, and body mass index of the user,
   wherein altering the appearance of the three-dimensional anatomical model is based on the physical data attributes including the hair color, eye color, skin tone, or complexion of the user, and
   wherein altering the appearance of the three-dimensional anatomical model includes user alignment of specific pick points on two-dimensional photographs of the user's face, and transformation of the two-dimensional photographs of the user's face into the custom three-dimensional model of the user's face and head based on the specific pick points;
   conducting, by the at least one processor, a predictive analysis of a future health condition of the user based on regression analysis of data derived from a medical history of the user and on sample data from patient populations;
   creating, by the at least one processor, a future anatomical model by altering an appearance of an external body and an appearance of an internal organ of the personalized anatomical model based on the predictive analysis; and
   displaying, by the at least one processor, the future anatomical model on a computer screen of the computer system.

2. The method of claim 1, further comprising mapping, by the at least one processor, three-dimensional models generated from radiographic imaging of at least a portion of the user's body to the three-dimensional anatomical model.

3. The method of claim 1, wherein the plurality of anatomical systems includes at least one of the following systems: (i) eyes and vision; (ii) ear, nose, and throat; (iii) teeth and mouth; (iv) skin, hair, and nails; (v) bones and muscles; (vi) lungs and breathing; (vii) heart, and blood; (viii) digestive; (ix) hormones; (x) urinary; (xi) reproductive; (xii) immune; and (xiii) brain and nerves.

4. The method of claim 1, wherein the physical attribute data further includes the user's age, gender, body type, fat-lean ratio, an extant medical condition, an inferred effect of a medication, extent of osteoporosis, known genetic polymorphisms, clothing size, or shoe size.

5. The method of claim 1, wherein the data derived from a medical history of the user used in the predictive analysis includes data relating to a diet of the user, a fitness routine of the user, a lifestyle behavior of the user, or a combination thereof.

6. The method of claim 1, further comprising displaying, by the at least one processor, information associated with a visual element of the personalized anatomical model.

7. The method of claim 6, wherein the information associated with the visual element includes a label, a high level description, a detailed description, diagnostic notes, laboratory results, temporal graphing, temporal analysis, an analysis of conditions, a photograph, an image, medical data, or a combination thereof.

8. The method of claim 6, wherein the visual element includes an anatomical system of the plurality of anatomical systems, a functional system, an organ, an organelle, a tissue, cells, or a combination thereof.

* * * * *